United States Patent [19]
Crowley

[11] Patent Number: 5,840,031
[45] Date of Patent: Nov. 24, 1998

[54] CATHETERS FOR IMAGING, SENSING ELECTRICAL POTENTIALS AND ABLATING TISSUE

[75] Inventor: Robert J. Crowley, Wayland, Mass.

[73] Assignee: Boston Scientific Corporation, Boston, Mass.

[21] Appl. No.: 475,896

[22] Filed: Jun. 7, 1995

Related U.S. Application Data

[62] Division of Ser. No. 86,523, Jul. 1, 1993, abandoned.

[51] Int. Cl.⁶ ..................................................... A61B 8/00
[52] U.S. Cl. ........................................... 600/440; 607/122
[58] Field of Search ........................ 128/660.03, 662.06, 128/654, 786, 642, 660.04, 660.05; 606/27; 607/122; 600/440

[56] References Cited

U.S. PATENT DOCUMENTS

| | | | |
|---|---|---|---|
| 4,249,539 | 2/1981 | Vilkomerson et al. | 128/660 |
| 4,407,294 | 10/1983 | Vilkomerson | 128/660 |
| 4,641,649 | 2/1987 | Walinsky et al. | 128/303.1 |
| 4,676,258 | 6/1987 | Inokuchi et al. | 128/804 |
| 4,709,698 | 12/1987 | Johnston et al. | 128/303.12 |
| 4,821,731 | 4/1989 | Martinelli et al. | 128/662.06 |
| 4,841,977 | 6/1989 | Griffith et al. | 128/660.03 |
| 4,951,677 | 8/1990 | Crowley et al. | 128/662.06 |
| 4,955,377 | 9/1990 | Lennox et al. | 128/401 |
| 5,000,185 | 3/1991 | Yock | 128/662.06 X |
| 5,054,492 | 10/1991 | Scribner et al. | 128/662.06 |
| 5,103,804 | 4/1992 | Abele et al. | 128/4 |
| 5,106,360 | 4/1992 | Ishiwara et al. | 600/2 |
| 5,121,750 | 6/1992 | Katims | 128/662.06 |
| 5,125,410 | 6/1992 | Misono et al. | 128/662.06 |
| 5,131,397 | 7/1992 | Crowley | 128/662.06 |
| 5,140,987 | 8/1992 | Schuger et al. | 128/642 |
| 5,156,151 | 10/1992 | Imran | 128/642 |
| 5,190,046 | 3/1993 | Shturman | 128/662.06 |
| 5,203,337 | 4/1993 | Feldman | 128/662.04 X |

(List continued on next page.)

OTHER PUBLICATIONS

Avitall et al., "The Physics and Engineering of Transcatheter Cardiac Tissue Ablation"; (date unknown).

The BBI Newsletter, "Interventional Electrophysiology Poised for Growth"; *The BBI Newsletter*; vol. 14, No. 9 Sep. 12, 1991.

Becker et al., "Radiofrequency Balloon Angioplasty Rationale and Proof of Principle"; pp. 810–817; *Invest. Radiol.*, 1988; 23.

Berns et al., "Feasibility of Radiofrequency–Powered, Thermal Balloon Ablation of Atrioventricular Bypass Tracts Via the Coronary Sinus"; Nov. 11–14, 1991.

(List continued on next page.)

*Primary Examiner*—Francis Jaworski
*Attorney, Agent, or Firm*—Lyon & Lyon LLP

[57] ABSTRACT

An acoustic imaging system for use within a heart has a catheter, an ultrasound device incorporated into the catheter, and an electrode mounted on the catheter. The ultrasound device directs ultrasonic signals toward an internal structure in the heart to create an ultrasonic image, and the electrode is arranged for electrical contact with the internal structure. A chemical ablation device mounted on the catheter ablates at least a portion of the internal structure by delivery of fluid to the internal structure. The ablation device includes a material that vibrates in response to electrical excitation, the ablation being at least assisted by vibration of the material. The ablation device may alternatively be a transducer incorporated into the catheter, arranged to convert electrical signals into radiation and to direct the radiation toward the internal structure. The electrode may be a sonolucent structure incorporated into the catheter, through which the ultrasound device is arranged to direct signals. An acoustic marker mounted on the catheter emits a sonic wave when electrically excited. A central processing unit creates a graphical representation of the internal structure, and superimposes items of data onto the graphical representation at locations that represent the respective plurality of locations within the internal structure corresponding to the plurality of items of data. A display system displays the graphical representation onto which the plurality of items of data are super-imposed.

27 Claims, 18 Drawing Sheets

U.S. PATENT DOCUMENTS

| | | |
|---|---|---|
| 5,211,165 | 5/1993 | Dumoulin et al. .................... 128/653.1 |
| 5,211,176 | 5/1993 | Ishiguro et al. .................... 128/662.06 |
| 5,222,501 | 6/1993 | Ideker et al. .................... 128/662.06 X |
| 5,281,215 | 1/1994 | Milder ........................................ 606/20 |
| 5,295,484 | 3/1994 | Marcus et al. ..................... 128/660.03 |
| 5,295,962 | 3/1994 | Crocher et al. ........................... 604/96 |
| 5,323,781 | 6/1994 | Ideker et al. ........................ 128/660.03 |
| 5,324,255 | 6/1994 | Passafaro et al. ......................... 604/49 |
| 5,325,860 | 7/1994 | Seward et al. ................. 128/660.03 X |
| 5,345,938 | 9/1994 | Nishiki et al. ................. 128/662.06 X |
| 5,345,940 | 9/1994 | Sewart et al. ...................... 128/660.03 |
| 5,368,035 | 11/1994 | Hamm et al. ...................... 128/662.06 |
| 5,372,138 | 12/1994 | Crowley et al. ................... 128/662.06 |
| 5,375,601 | 12/1994 | Nicholas et al. .................... 128/662.06 |
| 5,383,460 | 1/1995 | Jang et al. .......................... 128/662.06 |
| 5,391,199 | 2/1995 | Ben-Haim ............................... 607/122 |
| 5,403,311 | 4/1995 | Abele et al. .............................. 606/49 |
| 5,433,198 | 7/1995 | DeSai ................................. 607/122 X |
| 5,464,016 | 11/1995 | Nicholas et al. ................... 128/662.06 |
| 5,540,679 | 7/1996 | Fram et al. ............................... 606/27 |

OTHER PUBLICATIONS

Bom, N. et al., "Early and Present Examples of Intraluminal Ultrasonic Echography," 1989, SPIE vol. 1068 Catheter–Based Sensing and Imaging Technology, pp. 146–150.

Borggrefe, "Catheter Ablation Using Radiofrequency Energy"; *Clinical Cardiol*. vol. 13, pp. 127–131, (1990).

Boston Scientific Corporation, "Anatomy and Physiology" brochure; (date unknown).

Boston Scientific Corporation, "Explorer™ Series Electrophysiology Mapping Catheters"; (date unknown).

Boston Scientific Corporation, "Explorer 360° Series Advanced Electrophysiology Mapping Catheters"; (date unknown).

Boston Scientific Corporation, "Gold Probe™—The Next Generation in Bipolar Hemostasis"; (date unknown).

Boston Scientific Corporation, "Polaris™ Series Steerable/Deflectable Tip Mapping Catheters"; (date unknown).

Boston Scientific Corporation, "The Soft Steerable Catheter system for Rapid G I Intubation for Decompression and Sampling"; Oct., 1978.

Buxton, "Catheter Ablation of Atrioventricular Bypass Tracts"; *Circulation*, pp. 1388–1390, vol. 79, No. 6, Jun., 1989.

Calkins et al., "Diagnosis and Cure of the Wolff–Parkinson–White Syndrome or Paroxysmal Supraventricular Tachycardias During a Single Electrophysiologic Test"; *N.E. Journal of Med.*, vol. 324, No. 23, Jun. 6, 1991.

Critelli, "Transcatheter Ablation of Tachyarrhythmias: An Evolving Therapeutic Procedure"; *Journal of Inter. Card.*, vol. 2, No. 4, 1989.

Crowley et al., "Optimized Ultrasound Imaging Catheters for Use in the Vascular System"; *Internatl. Journ. of Card. Imag.*, 4: 145–151; 1989.

Crowley et al., "Ultrasound Guided Therapeutic Catheters: Recent Developments and Clinical Results"; *Interntl. Journ. Card. Imag.*, 6: 145–156, 1991.

Ellis et al., "Ultrasonic Imaging Catheter"; Microvasive, Inc.; 1988.

Frank et al., "Implantable Cardioverter–Defibrillators: Alternative Treatment for Ventricular Tachyarrhythmias"; *Coronary Artery Disease*, Mar. 1992, vol. 3, No. 3.

Haywood, "Dual IBAD Makes good Coatings"; (date unknown).

Jackman et al., "Catheter Ablation of Accessory Atrioventricular Pathways (Wolff–Parkinson–White Syndrome) by Radiofrequency Current"; *N.E. Journ. of Med.*, vol, 324, No. 23, Jun. 6, 1991.

Lesh, "Application of Ultrasound Imaging to Catheter Ablation of Cardiac Arrhythmias"; *Biomedical Business International*; (date unknown).

Mahomed et al., "Surgery for Wolff–Parkinson–white Syndrome"; *Coronary Artery Disease*, vol. 3, No. 3, Mar. 1992.

McGuire et al., "Surgical Techniques for the Cure of Atrioventricular Junctional Reentrant Tachycardia"; *Coronary Artery Disease*, Mar. 1992, vol. 3, No. 3.

McMath, "Percutaneous Laser Balloon Coagulation of Accessory Pathways"; *SPIE*, vol. 1425, pp. 165–169, 1991.

Saksena et al., "Low–Energy Transvenous Ablation of the Canine Atrioventricular Conduction System with a Suction Electrode Catheter"; *Circulation*; pp. 394–403; vol. 76, No. 2, Aug. 1987.

Schuger et al., "Long–Term Effects of Percutaneous Laser Balloon Ablation from the Canine Coronary sinus"; *Circulation*; vol. 86, No. 3, pp. 947–954; Sep. 1992.

Schuger et al., "Percutaneous Transcatheter Laser Balloon Ablation from the Canine Coronary Sinus: Implications for the Wolff–Parkinson–White Syndrome"; Lasers in Surgery and Medicine 10:140—148 (1990).

Selle, "Definitive Surgery for Postinfarction Ventricular Tachycardia"; *Coronary Artery Disease*, Mar. 1992 vol. 3, No. 3, pp. 204–209.

Sung, "Arrhythmias and the Autonomic Nervous System"; *Cardio*, pp. 77–80; Sep. 1987; Nov.—Dec., 1986, Part II, pp. 1396–1402.

Tarjan et al., "An Experimental Device for Low–Energy Precise Ablation of AV Conduction", *PACE*, vol. 9.

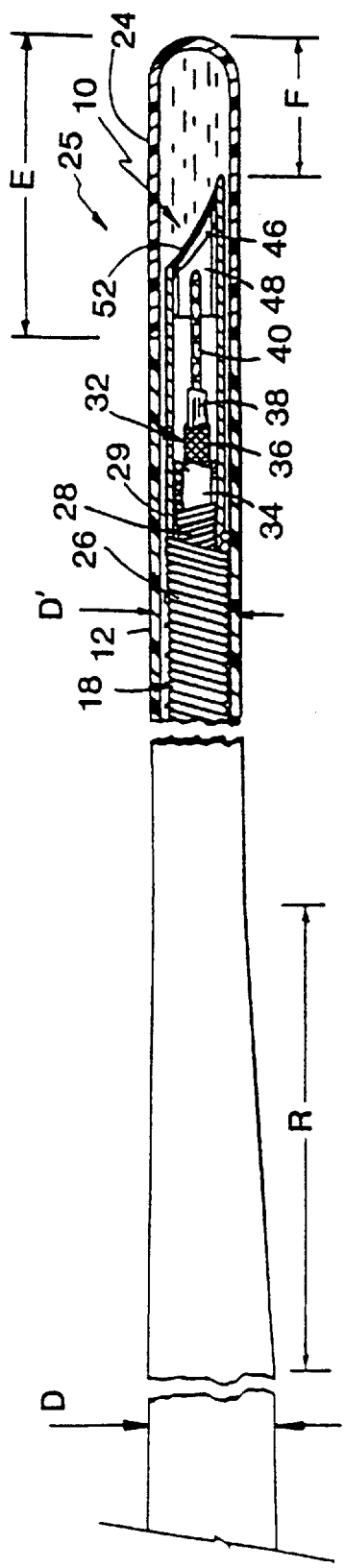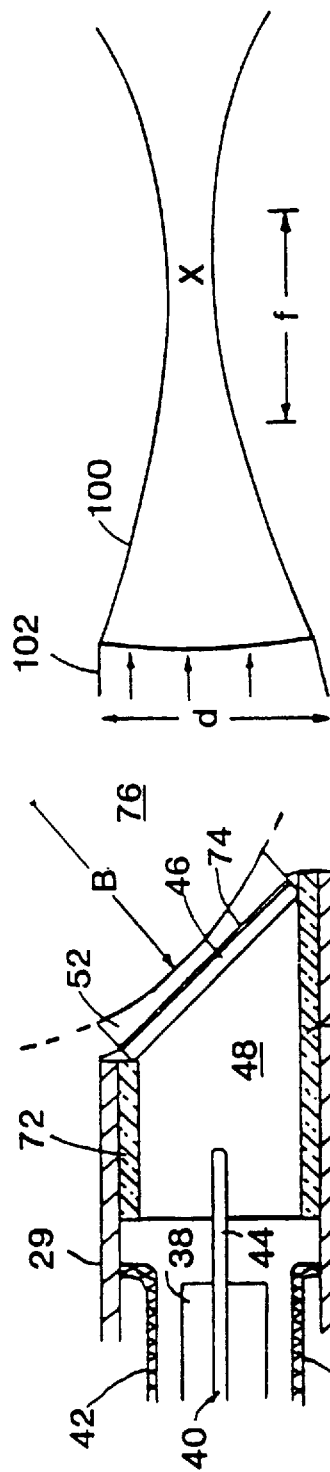

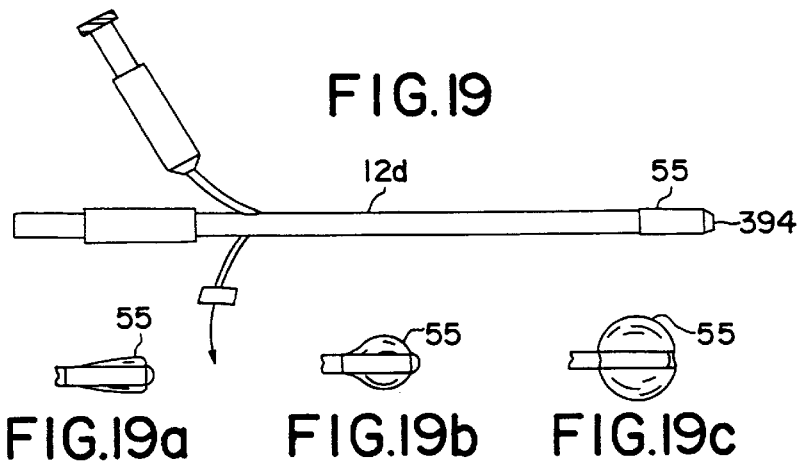
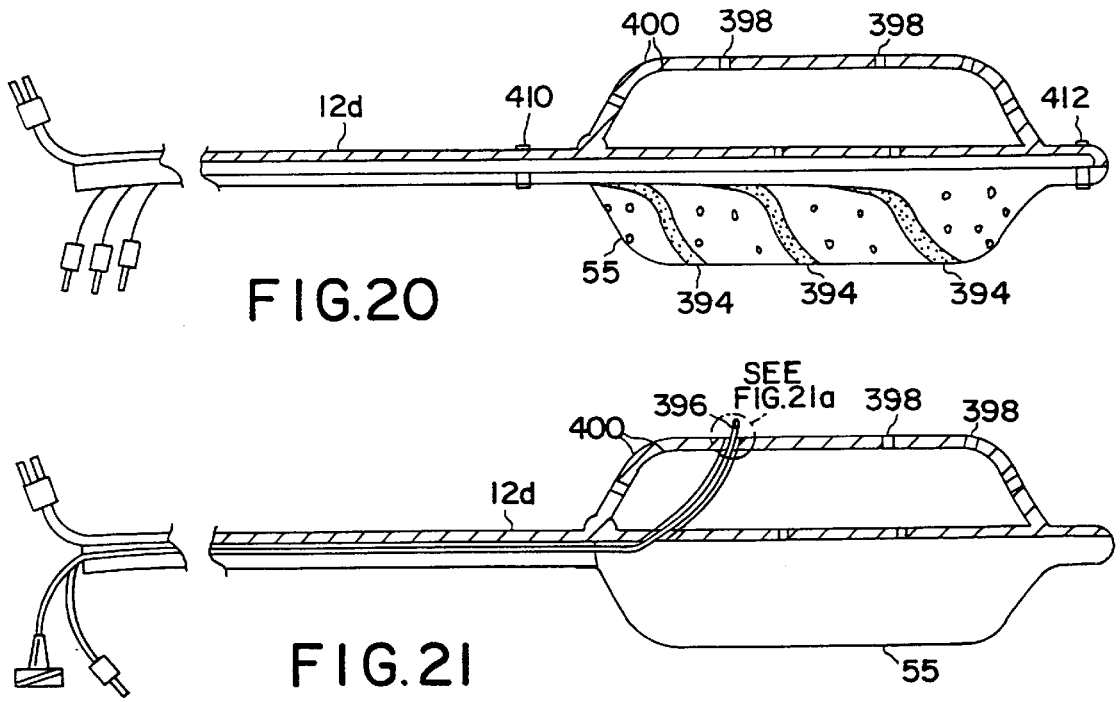
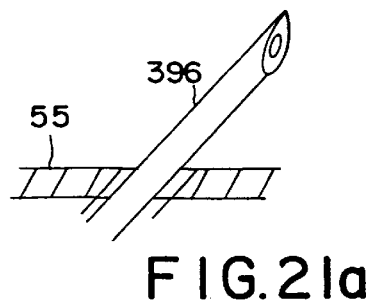

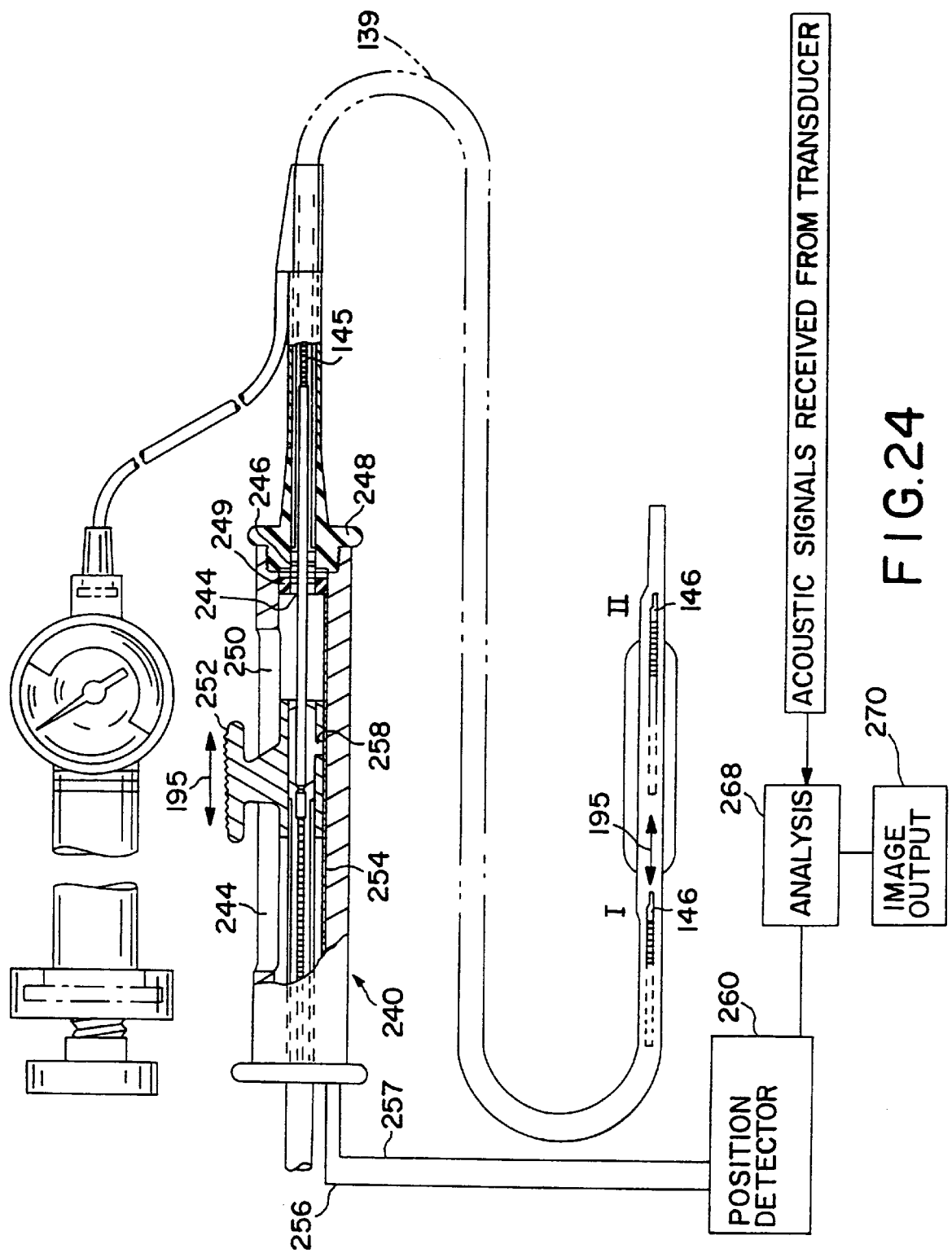

CATHETERS FOR IMAGING, SENSING ELECTRICAL POTENTIALS AND ABLATING TISSUE

This application is a divisional of U.S. application Ser. No. 08/086,523, filed Jul. 1, 1993 and now abandoned. The entire disclosures of U.S. Pat. No. 4,951,677 and U.S. Pat. No. 5,421,338 are hereby incorporated herein by reference.

BACKGROUND OF THE INVENTION

The action of the human heart is controlled by propagation of electrical activity in various regions of the heart. The presence of abnormal accessory pathways in the heart can lead to conditions such as ventricular tachycardia and atrial flutter. These conditions are very common. Approximately 20% of the population will have some type of electrical disturbance activity in the heart during their lifetimes.

Physicians have found that they can detect malfunctions of the heart by probing the heart with a catheter fitted with one or more electrodes and having steering capability, measuring voltages within the heart, and observing the waveforms. Once a physician understands how the electrical activity of the heart is operating he can, if he wishes to do so, choose to "disconnect" certain portions of the heart electrically by the process of ablation. If multiple electrode are used, the catheter can make multiple readings simultaneously when it is curved inside the heart. Thus, the use of multiple electrodes shortens the time required to map the heart.

The electrical activity of the heart is detected and read in accordance with a mapping procedure to determine the presence of abnormal accessory pathways in the heart. A typical mapping procedure involves using electrophysiology sensing electrodes mounted on a catheter as remote-controlled voltage-testing probes to test various locations in the heart.

The process of ablation is a destructive process in which the catheter is used to burn a certain section of the heart which stops the propagation of an electrical signal from one portion of the heart to another. Alternate means to perform ablation have been to inject a chemical such as ethanol in specific regions of the heart, to apply very cold temperatures in a process called cryo-ablation, and to use sonic energy, which is sometimes referred to as ultrasonic ablation. The ablation process may alternatively consist of applying low-frequency RF energy to the heart tissue in order to create a burn. This burn will cause the tissue to heat up and desiccate and finally necrose.

Electrophysiology catheters are typically positioned at various positions in the heart under x-ray guidance. The x-rays show the catheter, and can also show the heart itself and thus the position of the catheter relative to the heart if dye injections are made. The clinician tries to visualize the position of the catheter in the heart in the various chambers. Electrical means are used to determine whether or not the electrode is in contact with the heart, and this information is shown on an EKG display. During the course of a typical procedure the operator will frequently return to one or more positions, and will look for particular waveforms that he sees from the sensing electrodes to determine whether the catheter has returned to the desired position. Typically, more than one catheter is used in a given procedure, and the catheters are constructed with steering or torquing devices that assist in positioning of the catheters within the heart.

The sensing or ablation electrodes of intracardiac catheters are typically made of tantalum, gold, or platinum. There can be as few as one or as many as five or more electrodes in a sensing and ablation catheter. Typical sensing and ablation catheters will have at least one tip electrode and two, three, or four ring electrodes proximal to the tip electrode. The proximal ring electrodes are typically spaced from the distal tip in two, three, or four-millimeter increments. The ring electrodes are generally bonded or crimped onto the catheter body or blended into the catheter body. The rings are sufficiently thick to have enough mechanical strength when crimped to adhere to the catheter shaft.

It is known that the injections of chemicals such as ethanol into the heart can produce a response which is similar to that produced when a burn is made in the heart. Basically, the injection of chemicals disrupts or cuts off electrical pathways in the heart by causing localized cell death.

SUMMARY OF THE INVENTION

In one aspect, the invention features an acoustic imaging system for use within a body of a living being, having an elongated, flexible catheter constructed to be inserted into the body, an ultrasound device incorporated into the elongated, flexible catheter, and an electrode mounted on a distal portion of the elongated, flexible catheter. There are a plurality of electrical conductors extending from a proximal portion of the elongated, flexible catheter to the distal portion. At least two of the plurality of electrical conductors are connected to the ultrasound device and at least one of the plurality of electrical conductors is connected to the electrode. The ultrasound device is arranged to direct ultrasonic signals toward an internal structure within the body for the purpose of creating an ultrasonic image of the internal structure, and the electrode is arranged for electrical contact with the internal structure imaged by the ultrasound device.

The invention enables precise control and directability of catheters used in electrophysiology procedures, with the aid of high resolution images that reveal the cardiac anatomy and the location of the catheter and electrodes relative to the various chambers of the heart, the valves, the annuluses of the valves, and the other areas of the heart. Electrophysiology catheters according to the invention can be used without x-ray guidance, thereby eliminating dye injections and prolonged exposure of the patient and clinician to x-rays during the procedure. The clinician need not rely on his own imagination when trying to visualize the position of the catheter in the various chambers of the heart, and need not struggle to read an EKG display to determine whether an electrode is in contact with heart tissue. Thus, the invention reduces the time that it takes to obtain a reliable reading from a particular region of the heart that can be identified with ultrasound. Moreover, the physician need not look for particular waveforms from a sensing electrode to determine whether the electrode has returned to a desired position in the heart, and can reposition the electrode quickly and precisely. Also, by reducing the time required for electrophysiology sensing procedures and enhancing the precision with which an electrode can be positioned within the heart, the invention reduces the need for the catheter to include a large number of electrodes in order to reduce the time required to map the heart.

If the electrode is used for ablation, the on-catheter imaging also ensures that the electrode makes adequate contact with the endocardium, which is important because even if the catheter is in a position that is good enough to record the cardiac electrical activity it may not be good enough to deliver sufficient current to the portion of the heart requiring the ablation. There is no need to look at the impedance between the electrode and the heart itself to determine whether the electrode is in actual contact with the heart and there is no uncertainty as to whether the electrode is only in contact with blood, which of course is an electrical conductor and which would boil without creation of a lesion at all.

The invention also enables monitoring of the ablation process once it begins. The desiccation of tissue can be monitored by ultrasound, and it is useful to be able to see with ultrasound the depth and the extent of the lesion that is formed in the ablation procedure.

In another aspect, the invention features an acoustic imaging system for use within a body of a living being, having an elongated, flexible catheter, an ultrasound device incorporated into the elongated, flexible catheter, and a chemical ablation device mounted on a distal portion of the elongated, flexible catheter. The ultrasound device is arranged to direct ultrasonic signals toward an internal structure within the body of the living being for the purpose of creating an ultrasonic image of the internal structure, and the chemical ablation device is arranged to ablate at least a portion of the internal structure imaged by the ultrasound device by delivery of fluid to the internal structure.

By providing a mode of ablation that does not require electrophysiology sensing electrodes to be used also as ablation electrodes, the invention lowers the current delivery requirement for electrophysiology electrodes in electrophysiology catheters. I.e., an electrophysiology electrode used solely for sensing need not be as good an electrical conductor as an electrophysiology electrode that is also used for ablation.

Another aspect of the invention features an acoustic imaging system for use within a body of a living being, having an elongated, flexible catheter, an ultrasound device incorporated into the elongated, flexible catheter, and an ablation device comprising a transducer mounted on the distal portion of the elongated, flexible catheter. The ultrasound device is arranged to direct ultrasonic signals toward an internal structure within the body for the purpose of creating an ultrasonic image of the internal structure. The transducer is constructed arranged to convert electrical signals into radiation and to direct the radiation toward the internal structure within the body for the purpose of ablating tissue. The ablation device is arranged to ablate at least a portion of the internal structure imaged by the ultrasound device.

Another aspect of the invention features a catheter system that includes an elongated, flexible catheter, an imaging system, a data collection system, a central processing unit, and a graphic display system. The imaging system is constructed and arranged to provide information from which a graphical representation of an internal structure within the body may be created. The data collection system is at least partially located on a distal portion of the elongated, flexible catheter, and is constructed and arranged to produce a plurality of items of data corresponding to a respective plurality of locations within the internal structure. The central processing unit is electrically connected to the imaging system and the data collection system, and is configured and arranged to create the graphical representation of the internal structure from the information provided by the imaging system, and to super-impose onto the graphical representation the plurality of items of data provided by the data collection system. The plurality of items of data are super-imposed at locations on the graphical representation that represent the respective plurality of locations within the internal structure corresponding to the plurality of items of data. The graphic display system is electrically connected to the central processing unit, and is constructed to display the graphical representation onto which the plurality of items of data are super-imposed.

By super-imposing items of data on a graphical representation of an internal structure such as the heart, the invention provides an improved way to display in a meaningful and readily understandable manner the substantial information that is stored and saved in connection with a mapping procedure.

Another aspect of the invention features an acoustic imaging system for use within a body of a living being, having an elongated, flexible catheter, an ultrasound device incorporated into the elongated, flexible catheter, and at least one sonolucent, electrically conductive structure incorporated into the elongated, flexible catheter. In one embodiment the sonolucent structure is an electrode imprinted onto the catheter shaft as a thin film. The ultrasound device is arranged to direct ultrasonic signals through the sonolucent, electrically conductive structure toward an internal-structure within the body for the purpose of creating an ultrasonic image of the internal structure.

By eliminating the thickness of ordinary metal ring electrodes bonded or crimped onto the body of a catheter, the invention enables an acoustic imaging electrophysiology catheter (capable of sensing, ablation, steering, and imaging) to have a profile that is small enough to permit easy access of several such catheters into the heart and to permit great maneuverability and flexibility of the catheters with minimal trauma to the patient. In particular, the ultrasound imaging device occupies considerable space in the assembly, and in order to make space for the ultrasound imaging device the electrical wires can be placed on the periphery of the catheter in accordance with the invention without adding substantially to the size of the catheter or interfering with imaging. The invention also allows an acoustic imaging electrophysiology catheter to be sufficiently flexible, because very thin traces do not add to the stiffness of the catheter in the way that individual wires sometimes do.

Another aspect of the invention features an ablation system for use within a body of a living being, having an elongated, flexible catheter, and an ablation device mounted on a distal portion of the elongated, flexible catheter, and a plurality of electrical conductors extending from a proximal portion of the elongated, flexible catheter to the distal portion. The ablation device includes a material that vibrates in response to electrical excitation, and the ablation device is constructed and arranged to cause ablation of at least a portion of an internal structure within the body. The ablation is at least assisted by vibration of the material.

Another aspect of the invention features a catheter system, having an elongated, flexible catheter, an acoustic imaging system constructed and arranged to direct ultrasonic signals toward an internal structure within the body for the purpose of creating an ultrasonic image of the internal structure, and constructed and arranged to provide the ultrasonic image, and an acoustic marker mounted on at least a distal portion of the elongated, flexible catheter. The acoustic marker is constructed to emit a sonic wave when the acoustic marker is electrically excited. The acoustic imaging system is constructed in a manner such that interference of the sonic wave emitted by the acoustic marker with the ultrasonic signals directed toward the internal structure by the acoustic imaging system causes an identifiable artifact to appear on the ultrasonic image of the internal body structure.

Another aspect of the invention features a method of ablating heart tissue. An elongated, flexible catheter is provided that has an ultrasound device and an ablation device incorporated into a distal portion thereof. The elongated, flexible catheter is inserted into a body of a living being, and the distal portion of the elongated, flexible catheter is introduced into the heart. The ultrasound device is positioned in the vicinity of an internal structure within the heart, and ultrasonic signals are directed from the ultrasound device toward the internal structure to create an ultrasonic image of the internal structure. The internal structure is ablated through use of the ablation device mounted on the distal portion of the elongated, flexible catheter.

BRIEF DESCRIPTION OF THE DRAWINGS

FIG. 4 is a longitudinal, cross-sectional view of the distal end of the assembled acoustic catheter.

FIG. 5 is a longitudinal sectional view of the transducer element of the catheter on a greatly magnified scale.

FIG. 6 is a diagrammatic representation of sound waves emanating from the acoustic lens of the catheter.

FIG. 8a is a cross-sectional view on an enlarged scale of a portion of FIG. 8.

FIG. 19 is a longitudinal view of a catheter sheath having a balloon in combination with an electrode for electrophysiology or cardiac ablation, and FIGS. 19a, 19b and 19c are longitudinal views of the distal portion of the catheter sheath shown in FIG. 19, illustrating stages of inflation of the balloon.

FIG. 20 is a partially cut-away longitudinal view of a catheter sheath having a balloon on which a set of electrodes is coated, the balloon being constructed of electrically excitable material and having a set of perfusion ports in-its wall.

FIG. 21 is a partially cut-away longitudinal view of a catheter sheath having a balloon through which a fluid-injection needle passes, the balloon being constructed of electrically excitable material and having a set of perfusion ports in its wall.

FIG. 21a is an enlarged view, partially in cross-section of the fluid-injection needle shown in FIG. 21 exiting through a wall of the balloon.

FIGS. 24, 25, and 26 are longitudinal views of alternative embodiments of acoustic imaging balloon catheters enabling relative axial positioning of the transducer and the balloon.

DETAILED DESCRIPTION

General Structure

Figure 1:
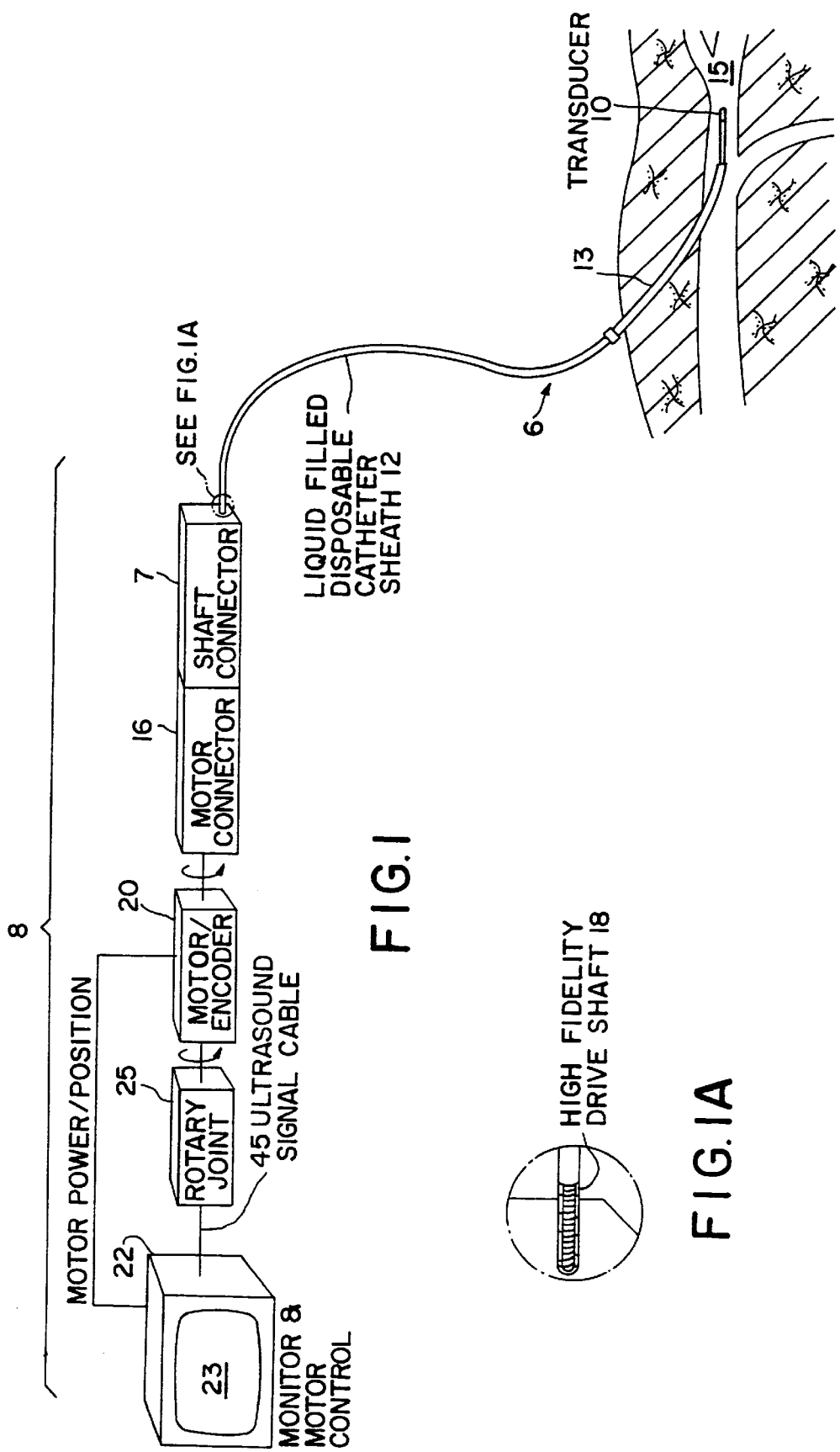
FIG. 1 is a schematic diagram of a system showing use of an acoustic catheter.

Referring to FIG. 1, a micro-acoustic imaging catheter 6 according to the invention is driven and monitored by a control system 8. The catheter is comprised of a disposable catheter sheath 12 (FIGS. 2 and 4) having a sound-transparent distal window 24 provided by dome element 25 (FIG. 4), in which is disposed a miniature, rotatable ultrasonic transducer 10 (FIGS. 3 and 4) driven by a special, high fidelity flexible drive shaft 18. A relatively rigid connector 11 is joined to the proximal end of the main body of the catheter sheath, adapted to be joined to a mating connector of drive and control system 8.

The catheter is adapted to be positioned within the heart by standard catheter procedures by guiding the flexible catheter through various blood vessels along a circuitous path, starting, for example, by percutaneous introduction through an introducer sheath 13 disposed in a perforation of the femoral artery 15.

Figure 2:
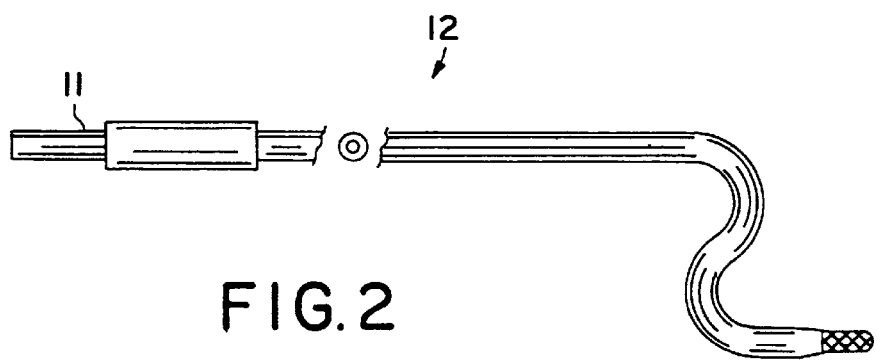
FIG. 2 is a side view of a disposable catheter sheath for the acoustic catheter.

Referring to FIG. 2, disposable catheter sheath 12 is a long tube, extruded from standard catheter materials, here nylon, e.g. with outer diameter, D, of 2 mm, wall thickness of 0.25 mm and length of 1 meter. Dome element 25, connected to the distal end of the tube, is a semi-spherically-ended cylindrical transducer cover constructed of material which is transparent to sound waves, here high impact polystyrene. This dome element has a thickness of approximately 0.125 mm and a length E of about 8 mm. For purposes described later herein, catheter sheath 12 in its distal region preferably tapers down over region R as shown in FIG. 4 to a narrowed diameter D' at its distal end, achieved by controlled heating and drawing of this portion of the original tube from which the sheath is formed. Catheter sheath 12 and acoustically transparent dome element 25 are adhesively bonded together.

Figure 3:
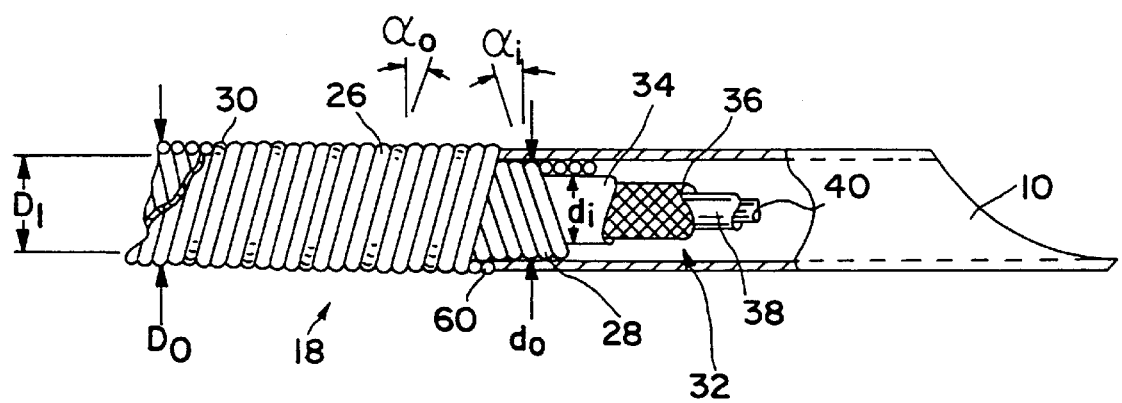
FIG. 3 is a longitudinal, partially cut away view of the distal end of the rotating assembly of the acoustic catheter.

Referring to FIGS. 3 and 4, the drive shaft assembly 18. is formed of a pair of closely wound multi-filar coils 26, 28 wound in opposite helical directions. These coils are each formed of four circular cross-sectional wires, one of which, 30, is shown by shading. Coils 26, 28 are soldered together at both the distal and proximal ends of the assembly in interference contact, here under rotational pre-stress. By also providing a pitch angle of greater than about 20°, a substantial part of the stress applied to the wire filaments of the coil is compression or tension in the direction of the axis of the filaments, with attendant reduction of bending tendencies that can affect fidelity of movement. There is also provision to apply a torsional load to the distal end of the assembly to cause the drive shaft to operate in the torsionally stiff region of its torsional spring constant curve, achieved by viscous drag applied to the rotating assembly by liquid filling the narrowed distal end of the catheter sheath (FIG. 4). Such loading, together with initial tight association of the closely wound filaments in the concentric coils, provides the assembly with a particularly high torsional spring constant when twisted in a predetermined direction. Thus, despite its lateral flexibility, needed for negotiating tortuous passages, the assembly provides such a torsionally stiff and accurate drive shaft that rotary position information for the distal end can, with considerable accuracy, be derived from measurement at the proximal end of the drive shaft, enabling high quality real-time images to be produced. Further description of the coils of the drive shaft and their condition of operation is provided below.

Coaxial cable 32 within coils 26, 28 has low power loss and comprises an outer insulator layer 34, a braided shield 36, a second insulator layer 38, and a center conductor 40. Shield 36 and center conductor 40 are electrically connected by wires 42, 44 (FIG. 5) to piezoelectric crystal 46 and electrically conductive, acoustical backing 48 respectively, of the transducer. Helical coils 26, 28, especially when covered with a highly conductive metal layer, act as an additional electric shield around cable 32.

Transducer crystal 46 is formed in known manner of one of a family of ceramic materials, such as barium titanates, lead zirconate titanates, lead metaniobates, and PVDFs, that is capable of transforming pressure distortions on its surface to electrical voltages and vice versa. Transducer assembly 10 is further provided with an acoustic lens 52. The radius of curvature B of lens surface 52 is greater than about 2.5 mm, chosen to provide focus over the range f (FIG. 6) between about 2 to 7 mm. The lens is positioned at an acute angle to the longitudinal axis of the catheter so that, during rotation, it scans a conical surface from the transducing tip, the angle preferably being between 10° and 80°, e.g., 30°. Transducer backing 48 is acoustically matched to the transducer element to improve axial resolution.

The transducer assembly 10 is supported at the distal end of the drive shaft by a tubular sleeve 29 which is telescopically received over a distal extension of the inner coil 28, as shown in FIG. 3.

Referring again to FIG. 4, the length, E, of dome element 25 is sufficient to provide headroom F for longitudinal movement of transducer 10 within the dome element as catheter sheath 12 and coils 26, 28 are twisted along the blood vessels of the body. In the untwisted state, transducer 10 is a distance F, about 2 to 3 mm, from the internal end surface of the dome element 25. The dome element, along with catheter sheath 12 is adapted to be filled with lubricating and sound-transmitting fluid.

Figure 7D:
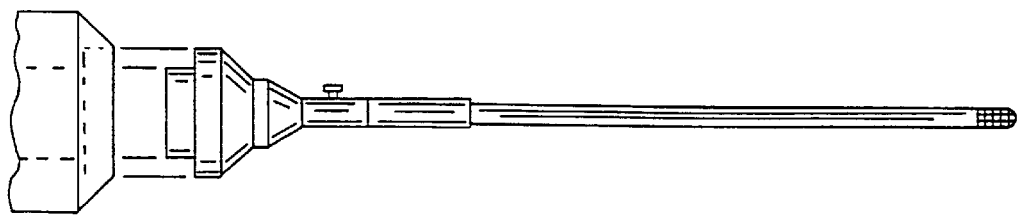
FIGS. 7–7d are longitudinal views of a catheter assembly illustrating steps in filling the sheath and assembling the acoustic catheter, the syringes shown in the figures being on a reduced scale.
Figure 7C:
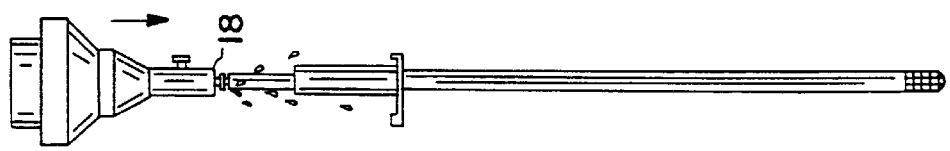
Figure 7B:
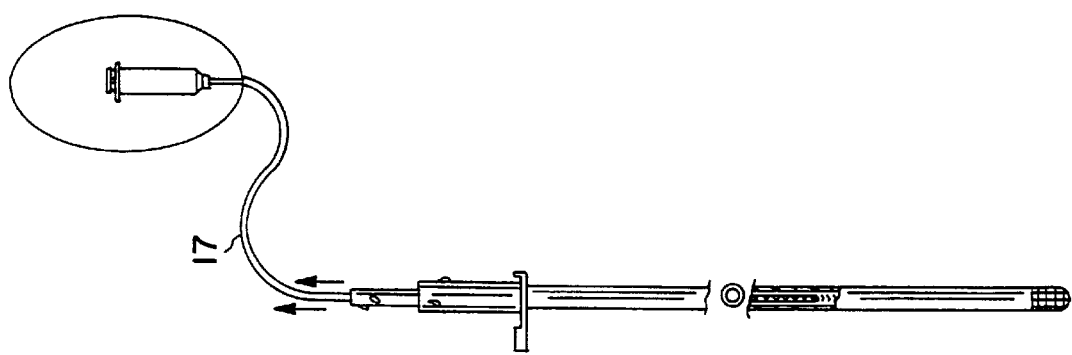
Figure 7A:
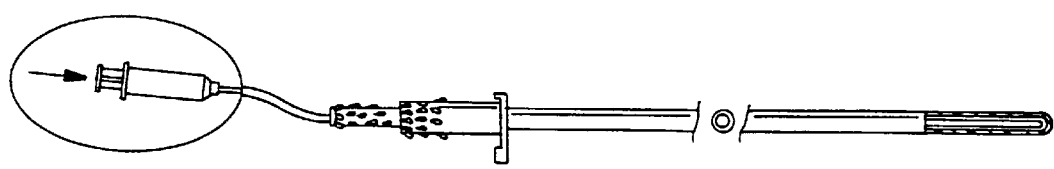
Figure 7:
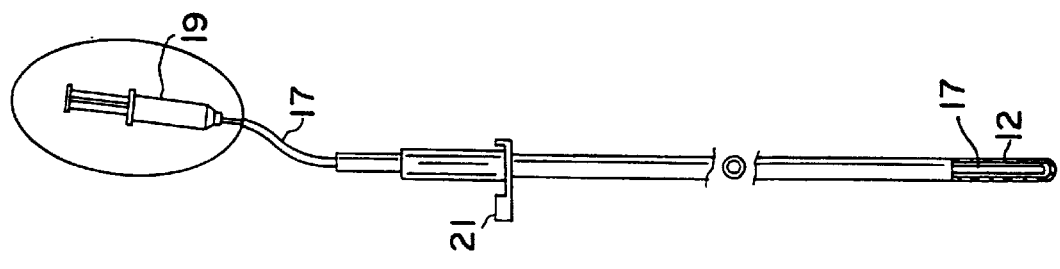

FIGS. 7–7b show the filling procedure used to prepare ultrasound catheter sheath 12 (or any of the other interchangeable sheaths described below) for attachment to the ultrasound imaging drive shaft and transducer assembly. A sterile, flexible filling tube 17 attached to a syringe 19 is filled with sterile water. This filling catheter is inserted into the ultrasound catheter sheath 12, all the way to the distal tip. The water is then injected until it completely fills and the excess spills out of the ultrasound catheter while held in a vertical position, see FIG. 7a. This expels air from the catheter which could impair good acoustic imaging. Continued pressure on the plunger of the syringe causes the flexible tube 17 to be pushed upward, out of catheter 12, FIG. 7b, leaving no air gaps behind. This eliminates the necessity to carefully withdraw the flexible filling tube at a controlled rate which could be subject to error. A holding bracket 21 is used to hold the catheter vertical during this procedure.

After the catheter sheath 12 is filled, the acoustic transducer 10 and shaft 18 are inserted, displacing water from the sheath 12, until the installed position, FIG. 7d, is achieved.

Figure 8:
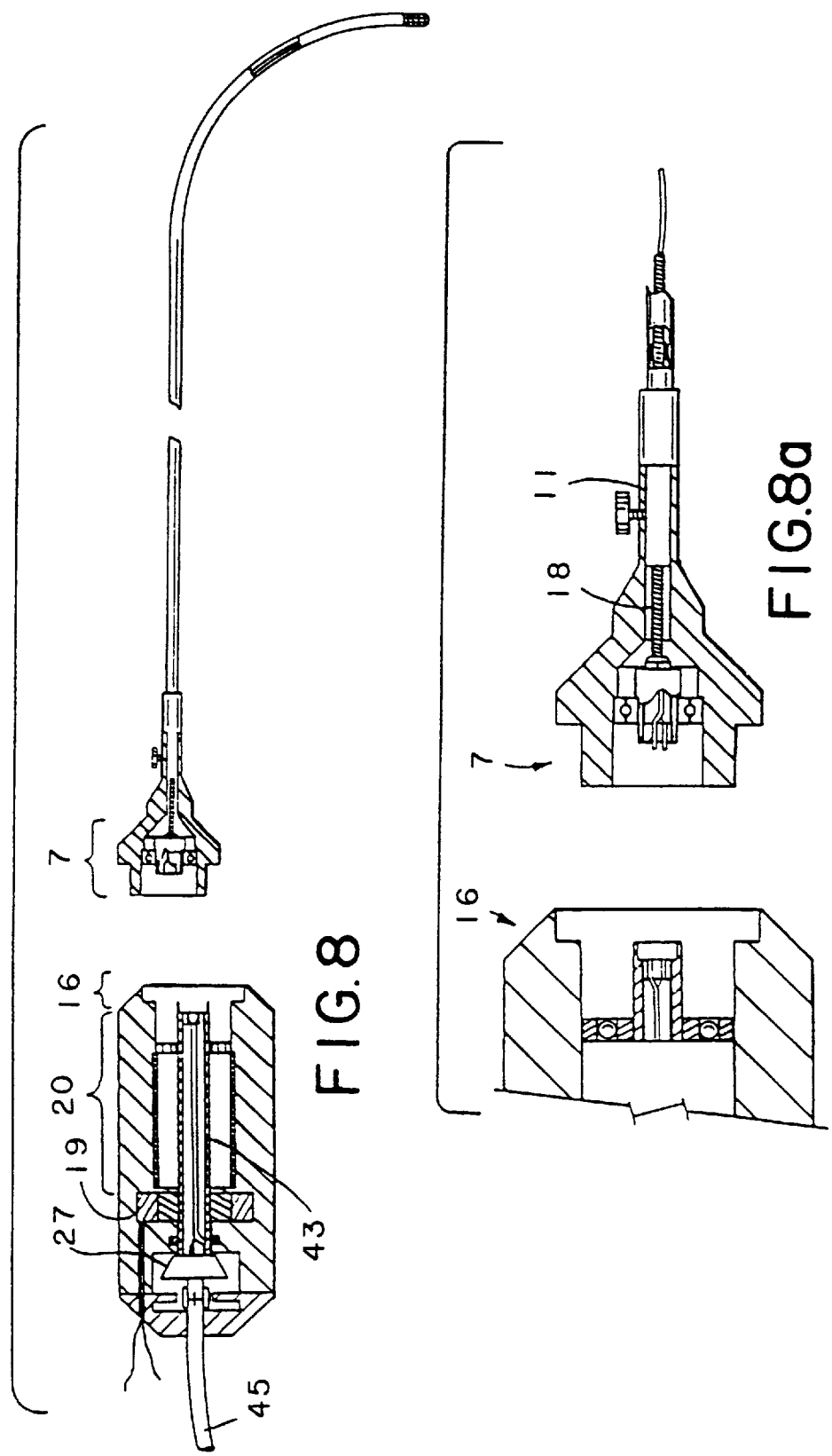
FIG. 8 is a cross-sectional view of the motor-connector assembly to which the catheter is connected.

FIGS. 8 and 8a (and FIG. 1, diagrammatically) show the interconnection arrangement for a connector 7 at proximal end of the acoustic catheter with connector 16 of the driving motor .20, and the path of the electric wires through the center shaft 43 of the driving motor. The center shaft and connector 16 rotate together, as do the wires that pass through the hollow motor shaft. The latter connect to a rotating electrical joint 27, which is held stationary at the back end and is connected to stationary coaxial cable 45 through a suitable connector such as a common BNC type. The enlarged view shows how the motor connector 16 and the driveshaft connector 7 mate when the two assemblies are pushed together, thereby making both electrical and mechanical contact. The catheter connector 7 is held in position by an ordinary ball bearing which provides a thrusting surface for the rotating connector 16 and driveshaft 18 while allowing free rotation. The disposable catheter sheath 12 includes an inexpensive, relatively rigid hollow bushing 11 of cylindrical construction that allows it to be slid into and held by means of a set screw in the housing that captures the non-disposable bearing, connector and driveshaft 18. The longitudinal and rotational position of hollow bushing 11 relative to the housing is adjustable. Drive shaft coil assembly 18, thus attached at its proximal end to connector 16 of drive motor 20, rotates transducer 10 at speeds of about 1800 rpm. The transducer 10 is electrically connected by coaxial cable 32 extending through coil assembly 18 and via the cable through the motor to the proximal electronic components 22 which send, receive and interpret signals from the transducer. Components 22 include a cathode ray tube 23, electronic controls for the rotary repetition rate, and standard ultrasonic imaging equipment; see FIG. 12. A rotation detector, in the form of a shaft encoder shown diagrammatically at 19, detects the instantaneous rotational position of this proximal rotating assembly and applies that positional information to components 22, e.g., for use in producing the scan image.

Because the rotation detector depends upon the position of proximal components to represent the instantaneous rotational position of the distal components, the rotational fidelity of the drive shaft is of great importance to this embodiment.

Manufacture and Assembly of the Drive Shaft

Referring to FIGS. 3 and 4, coils 26, 28 are each manufactured by winding four round cross-section stainless steel wires of size about 0.2 mm, so that $D_o$ is about 1.3 mm, $D_i$ is about 0.9 mm, $d_o$ is about 0.9 mm and $d_i$ is about 0.5 mm. The coils are closely wound with a pitch angle $\alpha_o$ and $\alpha_i$ where $\alpha_o$ is smaller than $\alpha_i$, e.g., 22½° and 31°, respectively. Flat wires having a cross-sectional depth of about 0.1 mm may also be used. The pitch angles are chosen to eliminate clearances 60 between the wires and to apply a substantial part of the stress in either tension or compression along the axis of the wire filaments. The coils, connected at their ends, are adapted to be turned in the direction tending to make outer coil 26 smaller in diameter, and inner coil 28 larger. Thus the two assemblies interfere with each other and the torsional stiffness constant in this rotational direction is significantly increased (by a factor of about 6) due to the interference. Operation of the driveshaft in the torsionally stiff region with enhanced fidelity is found to be obtainable by adding a torsional load to the distal end of the rotating assembly of the catheter. The importance of rotational fidelity and details of how it is achieved warrant further discussion.

For ultrasound imaging systems, the relative position of the ultrasound transducer must be accurately known at all times so that the return signal can be plotted properly on the display. Any inaccuracy in position information will contribute to image distortion and reduced image quality. Because position information is not measured at the distal tip of the catheter, but rather from the drive shaft at the proximal end, only with a torsionally stiff and true drive shaft can accurate position information and display be obtained.

Furthermore, it is recognized that any drive shaft within a catheter sheath will have a particular angular position which is naturally preferred as a result of small asymmetries. Due to this favored position, the shaft tends, during a revolution, to store and then release rotational energy, causing non uniform rotational velocity. This phenomenon is referred to as "mechanical noise" and its effect is referred to as "resultant angular infidelity" for the balance of this explanation.

According to the present invention, use is made of the fact that suitably designed concentric coils interfere with each other, as has been mentioned previously. When twisted in one direction, the outer layer will tend to expand and the inner layer contract thus resulting in a torsional spring constant which is equal only to the sum of the spring constants of each of the two shafts. When, however, twisted in the opposite direction, the outer layer will tend to contract while the inner layer will expand. When interference occurs between the inner and outer layers the assembly will no longer allow the outer coil to contract or the inner to expand. At this point, the torsional spring constant is enhanced by the interference between the shafts and the torsional spring constant is found to become five or ten times greater than the spring constant in the "non-interference" mode.

Figure 9:
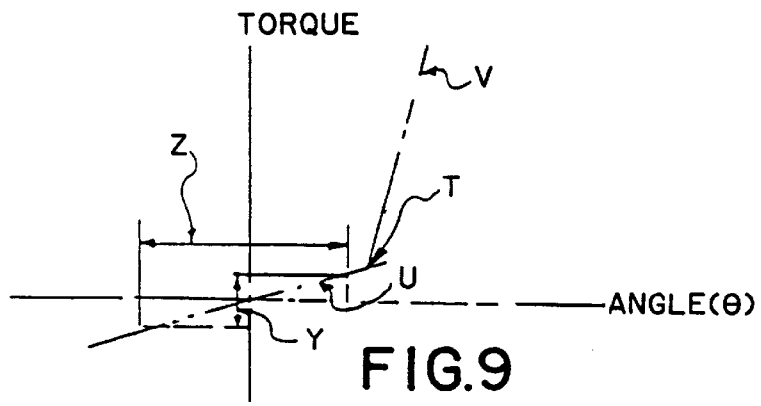
FIGS. 9, 10 and 11 are graphical representations of torque in relation to angular deflection.

Referring to FIG. 9, the relationship between torque and angular deflection for such a coil assembly is shown, assuming one end fixed and torque applied at the opposite end. 'Y' represents mechanical noise; 'Z' resultant angular infidelity; 'T' the interference point; the slope of the line 'U', the torsional spring constant (TSC) without interference (i.e., the sum of the torsional spring constant of each of the two coils); and the slope of the line 'V', the TSC with interference. Thus, TSC is shown to increase dramatically at the interference point.

Figure 10:
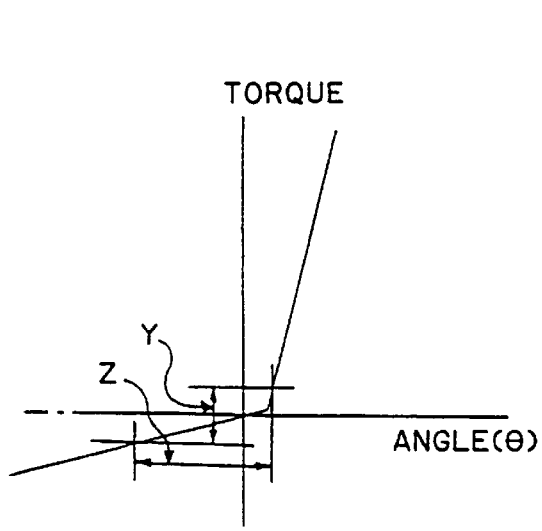

Referring to FIG. 10, by pre-twisting the shafts relative to one another and locking their ends together in a pre-loaded assembly, the interference point is moved to be close to the rest angle and resultant angular infidelity, Z, is reduced in the given direction of rotation.

Figure 11:
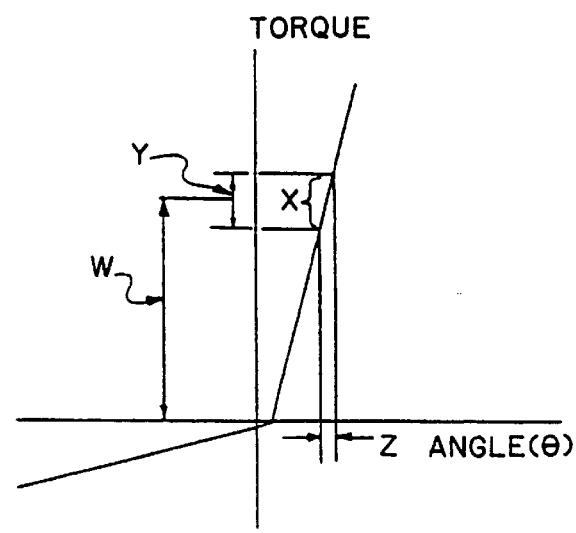

To improve upon this effect even further, dynamic frictional drag is intentionally introduced at the distal end of the shaft to raise the level of torque being continually applied to the system. This ensures operation of the shaft in the region of the high torsional spring constant or "interference" mode throughout its length, producing a rotationally stiffer shaft. This is shown in FIG. 11, where 'W' is dynamic load and 'X' is the region of operation. The use of such dynamic drag is of particular importance in certain catheters of small diameter, e.g. with outer diameter less than about 2 mm.

To form inner coil 28, four individual wires are simultaneously wound around a mandrel of about 0.5 mm outer diameter. The free ends of this coil are fixed, and then four wires are wound in opposite hand directly over this coil to form the outer coil 26. The wires are wound under moderate tension, of about 22.5 gm/wire. After winding, the coils are released. The inner mandrel, which may be tapered or stepped, or have a constant cross-sectional diameter, is then removed. The wire ends are finished by grinding. One end is then soldered or epoxied to fix the coils together for a distance of less than 3 mm. This end is held in a rigid support and the coils are then twisted sufficiently, e.g. ¼ turn, to cause the outer coil to compress and the inner coil to expand, causing the coils to interfere. The free ends are then also fixed.

The coil assembly 18 is generally formed from wires which provide a low spring index, that is, the radius of the outer coil 26 must be not more than about 2.5 to 10 times the diameter of the wires used in its construction. With a higher index, the inner coil may collapse. The multi-filar nature of the coils enables a smaller diameter coil to be employed, which is of particular importance for vascular catheters and other catheters where small size is important.

After the coil assembly is completed, coaxial cable 32 is inserted within the inner coil. The cable may be silver-coated on braid 36 to enhance electrical transmission properties. It is also possible to use the inner and outer coils 26, 28 as one of the electrical conductors of this cable, e.g. by silver coating the coils.

Referring back to FIGS. 3 and 5, to form transducer 10, wire 42 is soldered to either side of electrically conducting sleeve 29 formed of stainless steel. Wire 44 is inserted into a sound absorbent backing 48 which is insulated from sleeve 29 by insulator 72. Piezoelectric element 46 of thickness about 0.1 mm is fixed to backing 48 by adhesive and electrical connection 74 is provided between its surface and the end of sleeve 29. Thus, wire 42 is electrically connected to the outer face of piezoelectric element 46, and wire 44 electrically connected to its inner face. Spherical lens 52, formed of acoustic lens materials is fixed to the outer surface of element 46.

Referring to FIGS. 4 and 7–7d, the completed drive shaft 18 and transducer 10 are inserted into disposable catheter sheath 12, positioning transducer 10 within acoustically transparent dome element 25, with liquid filling the internal open spaces. The catheter thus prepared is ready to be driven by the drive assembly; see FIG. 8.

During use, rotation of drive shaft 18, due to exposure of the helical surface of the outer coil to the liquid, tends to create helical movement of the liquid toward the distal end of the sheath. This tends to create positive pressure in dome element 25 which reduces the tendency to form bubbles caused by out-gassing from the various surfaces in this region.

As has been mentioned, it is beneficial to provide added drag friction at the distal end of the rotating drive shaft 18 to ensure operation in the torsionally stiff region of the torsional spring constant curve. It is found that this may be done by simply necking down the distal portion of the catheter sheath 12, as shown in FIG. 4 to provide a relatively tight clearance between the distal portion of the shaft 18 and the inner surface of the sheath, to impose the desired degree of viscous drag. As an alternative, the dynamic drag may be provided by an internal protrusion in catheter sheath 12 to create a slight internal friction against drive shaft 18.

The acoustic catheter may be constructed so that it may be preformed prior to use by standard methods. Thus, if the investigator wishes to pass the catheter through a known tortuous path, e.g., around the aortic arch, the catheter can be appropriately shaped prior to insertion. Such preformation can include bends of about 1 cm radius and still permit satisfactory operation of the drive shaft.

Electronics

Figure 12:
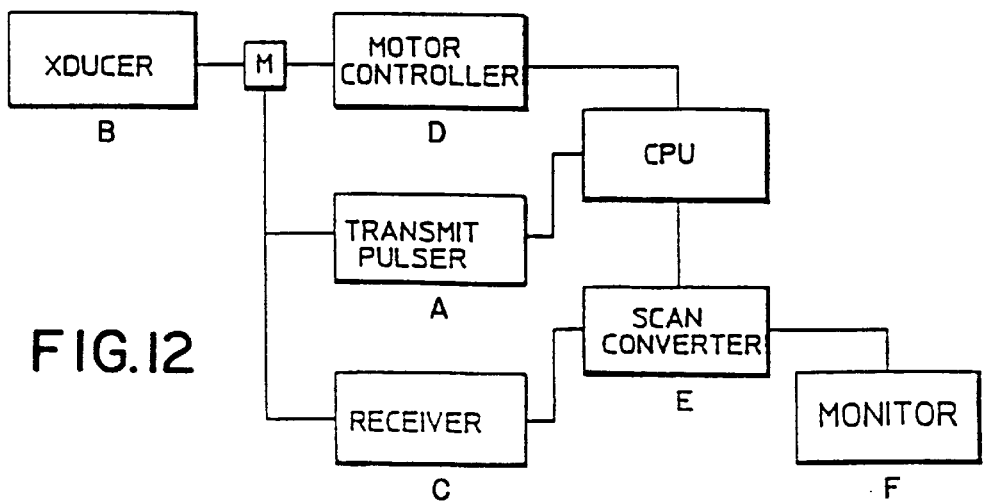
FIG. 12 is a block diagram of the electronic components useful with the acoustical catheter.

FIG. 12 is a block diagram of the electronics of a basic analog ultrasound imaging system used with the acoustical catheter. The motor controller (D) positions the transducer B for the next scan line. The transmit pulsed (A) drives the ultrasound transducer. The transducer (B) converts the electrical energy into acoustic energy and emits a sound wave. The sound wave reflects off various interfaces in the region of interest and a portion returns to the transducer. The transducer converts the acoustic energy back into electrical energy. The receiver (C) takes this wave-form and gates out the transmit pulse. The remaining information is processed so that signal amplitude is converted to intensity and time from the transmit pulse is translated to distance. This brightness and distance information is fed into a vector generator/ scan converter (E) which along with the position information from the motor controller converts the polar coordinates to rectangular coordinates for a standard raster monitor (F). This process is repeated many thousands of times per second.

By rotating the transducer at 1800 rpm, repeated sonic sweeps of the area around the transducer are made at repetition rate suitable for TV display, with plotting based upon the rotary positional information derived from the proximal end of the device. In this way a real time ultrasound image of a vessel or other structure can be observed.

Due to its rotational fidelity, the device provides a relatively high quality, real time image of heart tissue. It is also possible to form 3-dimensional images using appropriate computer software and by moving the catheter within the heart.

Selectable Catheter Sheaths

A wide variety of novel disposable catheter sheaths can be substituted for catheter sheath 12 and used in the system.

Figure 13:
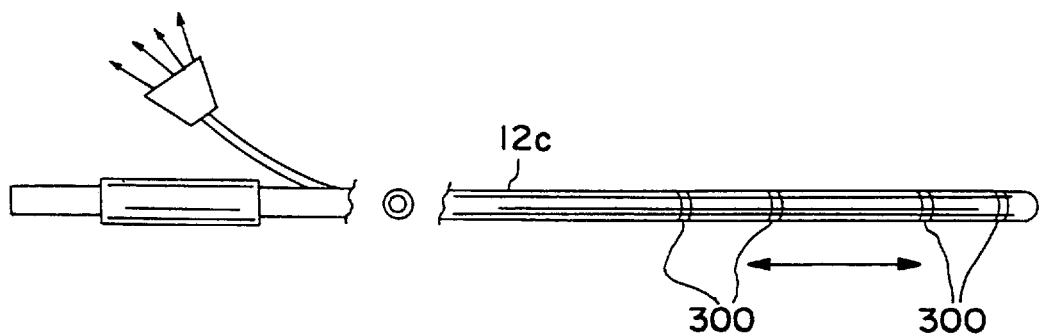
FIG. 13 is a longitudinal view of an acoustic imaging catheter sheath having electrodes for electrophysiology or cardiac ablation mounted on the catheter sheath.

FIG. 13 shows a flexible, disposable catheter sheath 12c on which are mounted a plurality of electrophysiology or ablation electrodes 300. Catheter sheath 12c may be combined with any of the technologies described below in connection with FIGS. 24, 25, and 26 to permit relative longitudinal movement between the transducer and electrodes 300.

Figure 14:
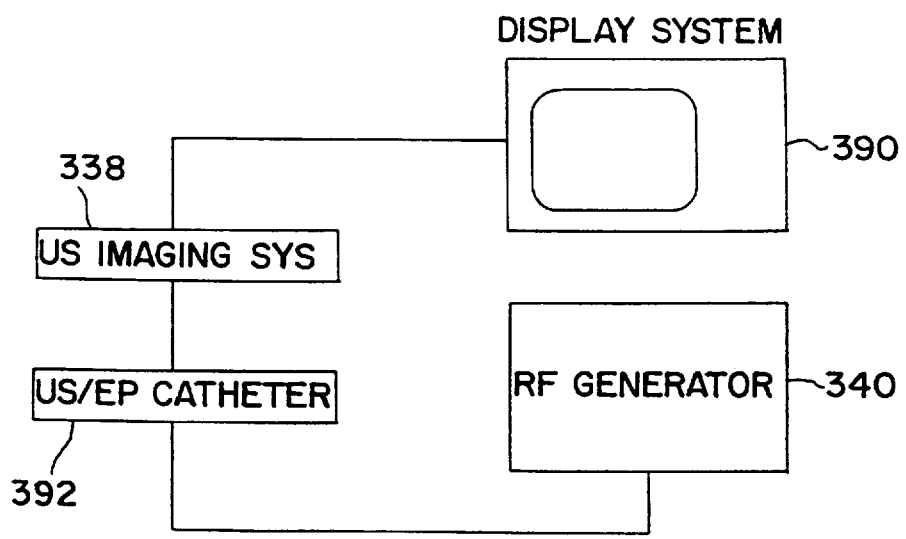
FIG. 14 is a block diagram of the principle components of an acoustic imaging and electrophysiology system that includes the catheter shown in FIG. 13.

With reference to FIG. 14, an ultrasound/ electrophysiology catheter 392 such as the one shown in FIG. 13 is connected to an ultrasound imaging system 338 that receives signals from the ultrasound transducer and transmits image data to display system 390 for display as an ultrasound image. RF generator 340 generates RF electrical signals for excitation of the ultrasound transducer or the electrodes. By observing in real time, on display system 390, the region of the heart near ultrasound/electrophysiology catheter 392, a physician can determine the position of the catheter sheath and electrodes relative to cardiac tissue and can also reposition catheter 392 at the same location at a later time. In order to reposition the catheter at the same location the physician either remembers the image or "captures" and stores the image using videotape or computer storage capabilities, so that the physician can compare the real time image with the captured or remembered image to determine whether the catheter has returned to the desired location.

Figure 15:
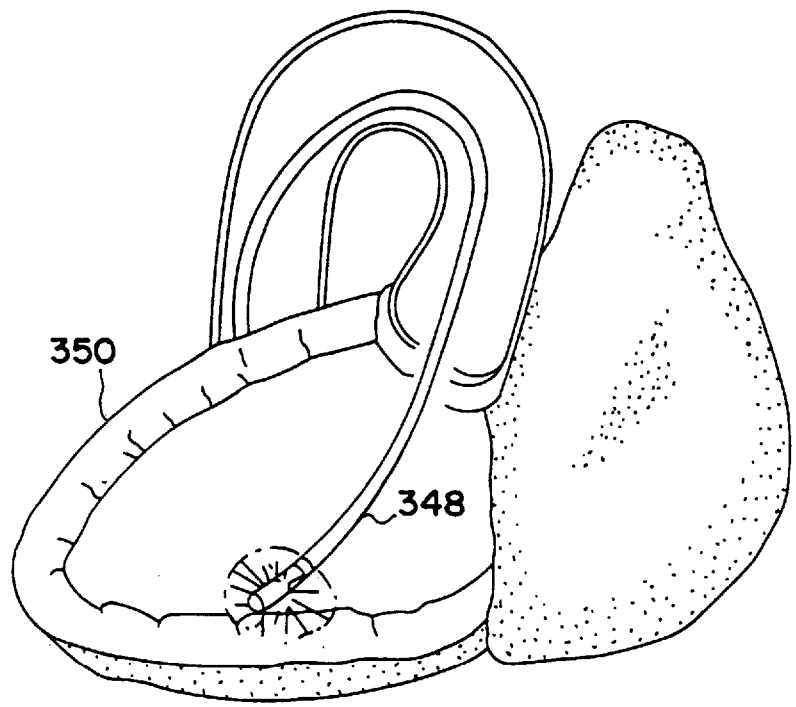
FIG. 15 is a partially cut-away view of a heart showing an acoustic imaging and electrophysiology catheter being used to image a chamber of the heart.
Figure 15A:
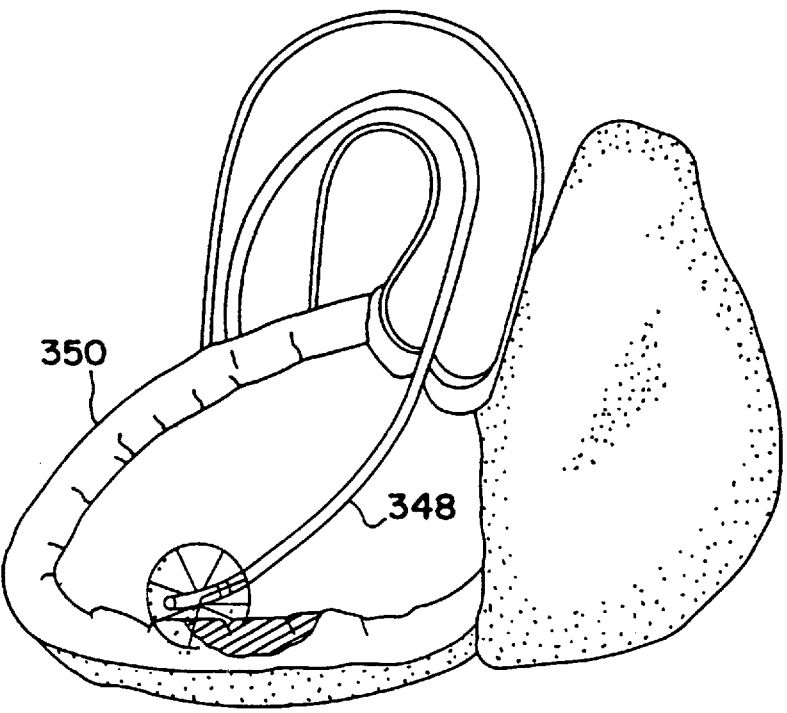
FIG. 15a is a partially cut-away view of a heart showing an acoustic imaging and electrophysiology catheter being used to image a portion of a chamber of the heart that has been ablated by means of the electrodes on the catheter sheath.

One of the questions that arises during the course of positioning the-catheter is whether or not a particular electrode is really in good electrical contact with the cardiac tissue. By visualizing the position of the electrode relative to the endocardium, the physician can make a judgment whether that electrode is in the proper position for a reliable reading. If not, the catheter can be readily repositioned by twisting the catheter and manipulating a steering wire, such as the one described in connection with FIG. 16 below, until the electrode or electrodes are in position. Without the use of visual information, the physician could continue to reposition the catheter in many locations of the heart and could compare these readings until he gets a picture in his mind of what the overall electrical activity of the heart is like. Using visual information, however, the physician can develop a better strategy that will tell him what areas of the heart he may ablate (using any of a variety of ablation techniques) in order to correct any perceived deficiencies in the electrical activity of the heart. FIGS. 15 and 15a show an acoustic imaging and electrophysiology catheter 348 being used to image a chamber of heart 350 before and after ablation of heart tissue, respectively.

Because the ultrasound transducer is being used to image points of actual contact of the surface of the electrode with cardiac tissue, it is necessary for the transducer to have close-up imaging capability, i.e., the ability to image from essentially the surface of the catheter outward. This close-up imaging capability is accomplished by using a very high frequency, such as 20 megahertz or higher. In certain circumstances, in which a compromise between close-up imaging and depth of penetration is desired, lower frequencies such as 10 megahertz could be used (there tends to be a trade-off between close-up and depth of penetration).

It is also possible to have more than one transducer on the same rotary shaft, one transducer being used for close-up imaging and the other being used for depth of penetration. Alternatively, there may be a single, multifrequency transducer, which is a step transducer having a piezo-electric element that has a series of concentric plates or zones of varying thicknesses. In one embodiment there would be two zones: a central zone that occupies half of the surface area of the transducer and that has thickness appropriate for generating acoustic waves in the order of 30 megahertz, and an annular zone around the central zone that has a greater thickness appropriate for generating acoustic waves around 10 megahertz. It is advantageous to have a single, multifrequency transducer rather than two different transducers because if a single, multifrequency transducer is used the user can select at will the depth of penetration desired and the frequency of operation desired without having to shift the position of the catheter, whereas if two transducers are used it may be necessary to shift the position of the catheter unless the two transducers oppose each other on opposite sides of the drive shaft.

The electrophysiological information obtained from electrodes 300 can be used to determine the location of catheter sheath 12c within the heart, as an alternative to using the ultrasound transducer. In particular, there are certain voltage patterns that are obtained during the electrophysiology procedure that identify certain landmarks in the heart.

If electrodes 300 are used for ablation, the imaging capability of the catheter can be used to determine immediately whether a specific change to the tissue has resulted from the ablation. Desiccation of tissue manifests itself as a brightening of the region of the ultrasound image corresponding to the location of the lesion. This brightening corresponds to increased reflection of ultrasonic signals.

Figure 16:
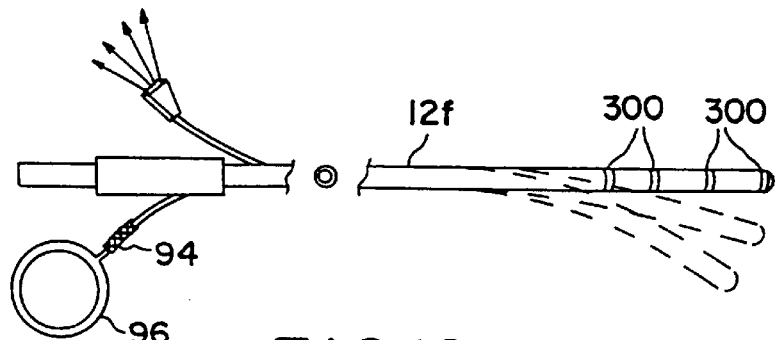
FIG. 16 is a longitudinal view of an acoustic imaging catheter sheath which is deflectable by actuation from the proximal end, and which includes electrodes for electrophysiology or ablation mounted on the catheter sheath.

FIG. 16 shows sheath 12f on which are mounted electrodes 300 for electrophysiology or ablation. Sheath 12f has a two lumen construction. The large lumen contains the transducer and drive shaft while the small lumen contains a wire 94. As shown, wire 94 is a deflecting or steering wire attached near the distal end, and is free to slide through its lumen under tension applied to ring 96 to cause the catheter to bend when pulled taut, thus providing a measure of control of the orientation of the distal end of the acoustic catheter while negotiating the passages of the body or the like. In another embodiment wire 94 may be a preformed stylet, which, when inserted through the second lumen, causes deflection of the tip.

Figure 17:
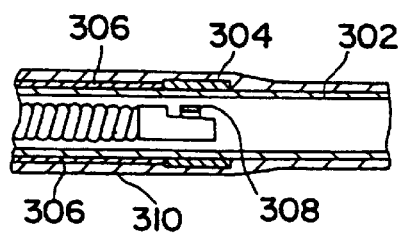
FIG. 17 is a longitudinal cross-sectional view of an acoustic imaging catheter sheath having a sonolucent metallic electrode and having a sonolucent metallic trace leading to the electrode.

FIG. 17 shows an acoustic imaging catheter sheath 302 having a sonolucent metallic electrode 304 for sensing electrical potentials or for ablation, and having a pair of sonolucent metallic traces 306 leading to electrode 304. Catheter sheath 302 has a diameter of nine french or less, and most preferably six french or less. Imaging transducer 308, because it is slidable (in accordance with any of the techniques described below in connection with FIGS. 24, 25, and 26), can be placed under or near electrode 304.

Because metal electrodes are very efficient reflectors of ultrasound energy, one would expect that there would be a high likelihood that reverberation artifacts would result when trying to image directly near, or as close as possible to, electrode 304 itself. Nevertheless, as described below, it is possible to make the electrode acoustically transparent, so that such reverberation artifacts do not tend to result, while the electrode is sufficiently conductive to perform the task of sensing and has a sufficiently low resistance to perform the function of ablation. The resistance from the proximal connector of the catheter to electrode 304 should be no more than 50 to 100 ohms for sensing and no more than 25 to 50 ohms for ablation. Otherwise, undue heating of the catheter could occur.

In one method of fabricating catheter sheath 302, a sonolucent tube of polyethylene is imprinted with conductive material to form electrode 304 and traces 306 leading to electrode 304. Electrode 304 and conductive traces 306 are made of aluminum that is deposited by vacuum deposition, which has been found to produce a low resistance, high reliability, conductive path that is sufficiently thin to allow ultrasound energy to pass through the aluminum almost unhindered. Then a covering 310, which is also sonolucent, is applied over the conductively treated catheter body to protect and seal electrode 304 and traces 306. Covering 310 includes micro-apertures filled with conductive material, as shown in FIG. 18a below. Because catheter sheath 302 and covering 310 are formed of a sonolucent material and because electrode 304 and traces 306 do not tend to reflect ultrasound energy, the presence of electrode 304 and traces 306 does not tend to create artifacts in the ultrasound image.

We now describe the vacuum deposition technique by which electrode 304 and traces 306 are deposited onto the sonolucent tube. First, the sonolucent tube, which is a single-lumen extrusion, is placed on a mandrel in a manner such that it can be held straight. Then a flat copper plate, such as is used for lithography, is photoetched over an area as long as the sonolucent tube and as wide as the circumference of the sonolucent tube in a manner such that a negative of the pattern of the traces and the electrode is imprinted upon the plate. The pattern is in the form of a waxy ink material rolled onto the copper plate. The sonolucent tube is then placed onto the copper plate at one side and rolled to the other side, which causes the sonolucent tube to be printed around its entire periphery in the manner of a printing roll.

The sonolucent tube is then placed into a chamber that is evacuated, with the mandrels being placed on a rotisserie so that they rotate. The sonolucent tube is coated with metal by a vacuum deposition process in which the metal is caused to melt in a graphite boat by induction heating and then the metal evaporates and deposits over the entire surface of the sonolucent tube. The metal covers both the areas where the ink is located and the areas where there is no ink. Then the sonolucent tube is removed from the chamber and is washed with a solvent such as trichlorethylene. This process washes away the ink with the aluminization that covers the ink, leaving the areas that are not printed with the ink intact with a thin aluminum coating.

The metal may alternatively be deposited onto the sonolucent tube by laser xerography, according to which a charge is put on the surface of the sonolucent tube, which tends to selectively accept aluminum ions or charged molecules as they are deposited. The metal is deposited by a vacuum deposition process in which the metal is caused to melt in a boat on which a charge has been placed, and the metal evaporates and charged metal particles deposit in the appropriate places on the sonolucent tube in accordance with xerographic techniques.

Alternative methods of depositing the metal onto the sonolucent tube include spraying a conductive paint onto a pattern on the sonolucent tube or spraying with a plasma gun (a small electron gun) that is capable of selectively depositing evaporated metal in specific areas on the sonolucent tube. The gun doesn't actually touch the surface of the sonolucent tube, but sprays the surface in a manner analogous to a very tiny airbrush.

If multiple electrode rings are formed on the sonolucent tube, some of the electrode rings may not completely encircle the sonolucent tube because certain traces would have to pass through these electrode rings. Alternatively, the traces and protective sonolucent coverings could be deposited as a multi-layer structure. For example, an electrode near the tip of the sonolucent tube could be deposited as a complete ring connected to a trace extending along the length of the sonolucent tube, and then a protective sonolucent covering could be placed over the deposited metal, and then a second deposition process could be performed to lay down a second ring, and so on as various layers of material are built up one on top of the other.

Another method of fabricating the catheter is to first print electrode 304 and traces 306 on a flat sheet of acoustically transparent material such as polyimide, and to roll that sheet up in a spiral like a jelly-roll and either place the sheet on the sonolucent tube or have the sheet be the sonolucent tube itself.

To prevent damage to the fragile electrodes and traces, a thin, acoustically transparent covering is placed over the aluminized or metallized catheter body. The covering may be nylon that is expanded and then shrunk onto the catheter body, or polyethylene that is shrunk onto the catheter body. Alternatively, the covering may be formed by spraying or dipping methods. Nylon and polyethylene are dialectic materials, and thus function as electrical insulators that would prevent the electrodes functioning when placed in proximity to the heart tissue were it not for the fact that microapertures are drilled through the protective coating.

Figure 18:
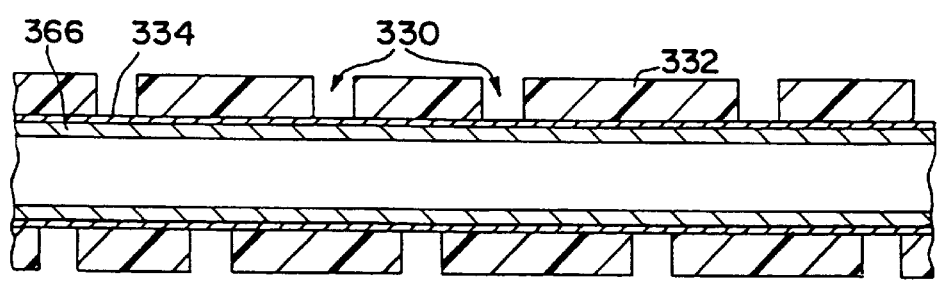
FIG. 18 is a longitudinal cross-sectional view of an acoustic imaging catheter sheath having a sonolucent metallic electrode and having a protective covering over the electrode with micro-apertures drilled through the covering.
Figure 18A:
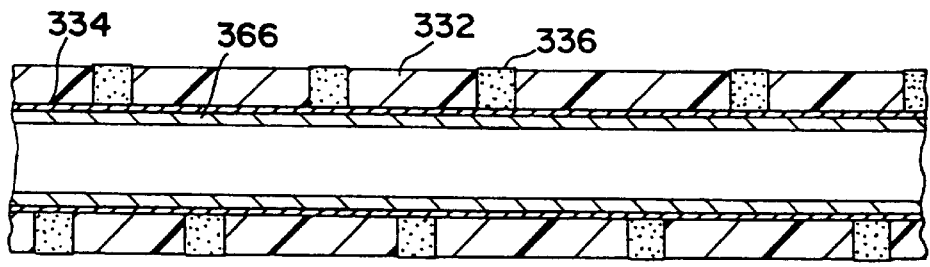
FIG. 18a is a longitudinal cross-sectional view of the acoustic imaging catheter sheath of FIG. 18 showing the micro-apertures filled with conductive material.

As shown in FIGS. 18 and 18a, the microapertures 330 in a protective coating 332 over a sonolucent electrode 334 and a sonolucent substrate 366 are very small holes, e.g., one micron in diameter or up to ten microns in diameter, drilled by UV eximer laser machining techniques, and are as thick as protective coating 332. The number of pulses of the eximer laser is selected in a manner such that the laser penetrates the thickness of the coating but does not to go below metal electrode 334; in any event, when the laser hits the metal it is just reflected anyway. The eximer laser technology could be provided by Resonetics, Nashua, New Hampshire 03063.

The density of microapertures 330 is as high as possible consistent with the strength of the materials. Generally, one needs to have 62,500 apertures in an area that is 3 square millimeters. The apertures can be formed very rapidly by indexing and also by optical steering while the catheter body is rotating. After these apertures are formed, the apertures are filled with a conductive jell material 336 such as that used for EKG electrodes at the place of manufacture of the catheter sheath. The conductive jell is then wiped clear of the catheter sheath. Alternatively, the apertures can be filled with an epoxy that includes tantalum, gold powder, or silver powder, or PVDF filled with a metal powder.

If the electrode is to be used for high-current ablation, the electrode-to-terminal resistance should be no more than 20 to 50 ohms, rather than the limit of 50 to 100 ohms that is acceptable for sensing purposes. The better conduction required for ablation can be achieved by applying additional gold plating over the areas that have been drilled with the micro-apertures, using masking and plating techniques or vacuum deposition, or using a gold plating solution.

An alternative to using the micro-apertures is to have the aluminized surfaces of the electrode simply exposed and to put protective covering over the traces but not the electrode. In order to minimize problems due to wear and handling of the electrodes, the exposed electrodes should be subjected to proper surface treatment and texturing.

FIGS. 19–19c show a catheter sheath 12d on which is mounted a balloon 55 very near the tip of catheter sheath 12d. The balloon is adapted to be pressurized with liquid, such as saline or water, or a gas, such as air, through the same lumen that holds the ultrasound imaging device, via an inflation opening in the wall of the catheter sheath. The balloon may be used to center or position the ultrasound device securely within a heart chamber and maintain its position away from an area of interest on a wall of the heart. The balloon in its collapsed or unpressurized state is easily inserted prior to positioning and may be accurately positioned by use of ultrasound imaging during initial placement. In other embodiments a separate lumen is provided for inflation of the balloon and/or the balloon is spaced from the distal end of the catheter.

If balloon 55 is filled with air at an appropriate point in time the balloon floats in a manner that assists the positioning of the catheter. For example, the balloon might float upwards from a lower ventricle to a higher atrium, for instance. The balloon physically moves the tip of the catheter from one location in the heart to another in a manner which is not possible with steering and pushing, although the balloon can be used in conjunction with such steering and pushing techniques. For example, the embodiment shown in FIG. 19 may be modified to include the steering wire shown in FIG. 16.

If balloon 55 is filled with air it can move either with the flow of blood or against the flow. If the balloon is inflated with liquid, such as saline, it becomes a flow-directed balloon that can travel only with the flow of blood. Such a flow-directed balloon is also useful to direct the catheter in the heart. Cardiologists know the path of flow in the heart very well, and if a cardiologist knows that the direction of flow in the heart is favorable for use of a flow-directed balloon, he can fill the balloon with fluid to cause it to move with the flow.

Thus, the air-filled or fluid-filled balloon simplifies the task of positioning the catheter, even if the catheter includes steering or torquing devices that assist in positioning of the catheter within the heart. Balloon 55 can also be used to perform other functions in the heart, such as valvularplasty.

In one embodiment balloon 55 is acoustically transparent, so that it doesn't obstruct the field of view of the acoustic imaging transducer. Materials such as cross-link polyethylene have high inflation strength, good biocompatability, processability, freedom of pinholes, and very low acoustic attenuation. These are commonly used balloon materials. It is also possible to use a latex or silicone balloon.

Frequently, when performing an electrophysiology sensing procedure or an electrode ablation procedure the clinician would like to apply pressure to the electrode and its adjacent heart tissue in order to assure a firm contact. Accordingly, in one embodiment, balloon 55 is an "opposing positioning balloon," i.e., a balloon that engages a wall of the heart or a structure such as the coronary sinus when the balloon is inflated in such a way as to cause one or more electrodes to press firmly against the cardiac tissue. FIG. 19 shows a single sensing or ablation electrode 394 mounted on the distal end of catheter sheath 12d, but in alternative embodiments there is more than one electrode. The electrode or electrodes may be mounted on catheter sheath 12d (as in FIG. 19), or on balloon 55 (as in FIG. 20), or on both catheter shaft 12d and balloon 55. With reference to FIG. 20, electrodes 394 can be printed on or placed on balloon 55 as rings or stripes by vacuum deposition, in a manner analogous to the method, described above, of creating acoustically transparent electrodes on a catheter sheath. Electrodes on catheter sheath 12d can also be created by this method, or can be simple metal rings of gold, silver, tantalum etc. FIG. 19 shows opposing positioning balloon 55 concentric to catheter sheath 12d, but in other embodiments the opposing positioning balloon is eccentric to the catheter sheath and the balloon is used to press the side of the catheter sheath itself the heart wall.

FIG. 21 shows balloon 55 combined with a chemical ablating needle 396, such as the one described below in connection with FIGS. 27 and 27a, that is constructed to inject a chemical into heart tissue to ablate the tissue. Needle 396 exits through a side wall of balloon 55, as shown in detail in FIG. 21a. Alternatively, needle 396 may exit catheter sheath 12d near balloon 55. Balloon 55 is made of an electrically excitable, acoustic generating material such as polyvinylidene fluoride (PVDF). During use, needle 396 is inserted into tissue under ultrasound guidance, the balloon is inflated, and the balloon material is electrically excited to aide the transfer of fluid from the needle into the adjacent tissue.

With reference to the embodiments shown in FIGS. 20 and 21, balloon 55, which is made of polyvinylidene fluoride (PVDF), has a number of small apertures 398 in the wall of the balloon. The inside of balloon 55 is connected to a source of a drug by means of a lumen extending through catheter sheath 12d. Apertures 498 are force fed with the drug while the balloon material is caused to vibrate. The vibrations feed the transfer of the fluid from balloon 55 into tissue with which the balloon is in contact. Radiopaque markers 410 and 412 are provided on catheter sheath 12d.

Referring still to FIGS. 20 and 21, PVDF is a material that is similar to mylar and can be fabricated in sheets and then formed into balloons that have wall thicknesses in the range from 1–2 thousands of an inch. In order to permit excitation of the balloon wall, the PVDF material has to be aluminized inside and out with aluminum layers 400. A very thin layer of aluminization is all that is needed because the electrically excitable balloon 55 is a high impedance device. During use, an alternating electric current is applied to balloon 55 at frequencies in the kilohertz to megahertz range (the frequency depending on the thickness of the balloon and the mode of excitation). The electric current causes the balloon to exhibit either transverse or planar vibration, which is therapeutically helpful in speeding the delivery of drugs and fluid into adjacent tissue. The vibration creates localized variations in pressure in the tissue, and given that fluid tends to migrate in the direction of areas of low pressure, the vibration helps migration of fluid through the tissue. The vibration also can create heat, which is known to improve the diffusion of some chemicals through tissue. Very high levels of vibration can be used as a massaging action to actually disrupt tissue and to directly create an ablative response.

Figure 22:
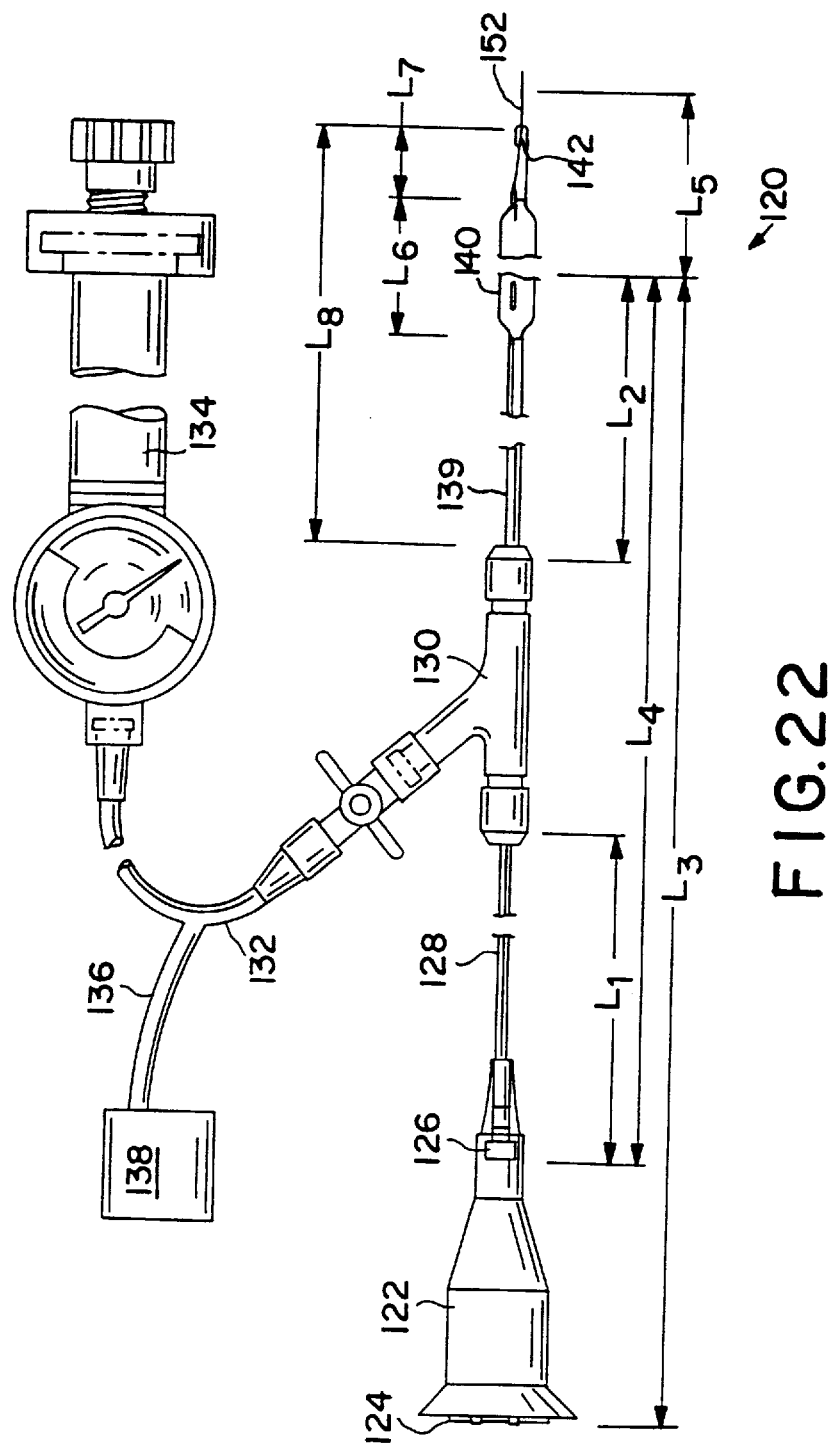
FIG. 22 is a longitudinal view of one embodiment of an acoustic imaging balloon catheter.

Referring to FIG. 22, a plan view of an acoustic imaging balloon catheter system is shown. This acoustic imaging balloon catheter system may include all of the features of the catheter system shown in FIGS. 19–19c, including one or more electrodes for electrophysiology or ablation mounted on the catheter sheath. The system 120 includes a boot member 122 including a ferrule member 124 at its proximal end, constructed to enable electrical and mechanical connection, as discussed for example with respect to FIGS. 8–8a, to the acoustic imaging control system as discussed for example with respect to FIG. 1, for transmitting rotary power and control signals to the acoustic imaging transducer held within the balloon catheter sheath 139 near balloon 140 and for receiving acoustical image signals from the transducer. The proximal end of the apparatus further includes a seal 126 (FIG. 23) which enables intimate but relatively frictionless contact with the portion of the rotating drive shaft.

Sheath 128 extends from the end of the seal 126 to a "Y" double flare compression fitting 130. Fitting 130 includes a side arm 132 for introduction of inflation fluid such as water or saline by means of a screw syringe 134 for inflation of balloon 140 near the distal end of the catheter 139.

Extending distally from the compression fitting 130 is catheter body sheath 139. The catheter may be adapted to track a guide wire which passes through a sonolucent saddle member beneath the balloon.

A rotating ultrasound transducer having a coil form drive shaft, as discussed herein above, is positioned on the central axis of the catheter sheath 139 at a position corresponding to the inflatable balloon 140. The catheter sheath 139 forms a sonolucent guide for the transducer and drive shaft. The catheter sheath is formed of a thin sonolucent material such as polyethylene to provide sufficient guidance for the drive shaft and transducer without causing excessive attenuation of the ultrasound signal emitted by the transducer. The catheter body material and the balloon material are in general selected to be sonolucent and have an acoustic impedance substantially matched to the body fluid, e.g., blood, to which the catheter is exposed, to minimize attenuation of the acoustic signals emitted and received from the transducer. Polyethylene is advantageous in that it has an acoustic impedance that substantially matches blood and saline, it is capable of withstanding high inflation pressures and is only slightly elastic, enabling a reliable balloon inflation diameter. It will be understood that the catheter may be formed having sonolucent regions corresponding to the location of the transducer while the rest of the catheter is not sonolucent, e.g., made of thicker material. Fluid communication between the balloon and the catheter may be provided through a port.

The balloon 140 which is preferably polyethylene, as discussed, may be mounted at its ends by, for example, melt-sealing. The balloon may also be secured by clips or the like as conventionally known.

Figure 23:
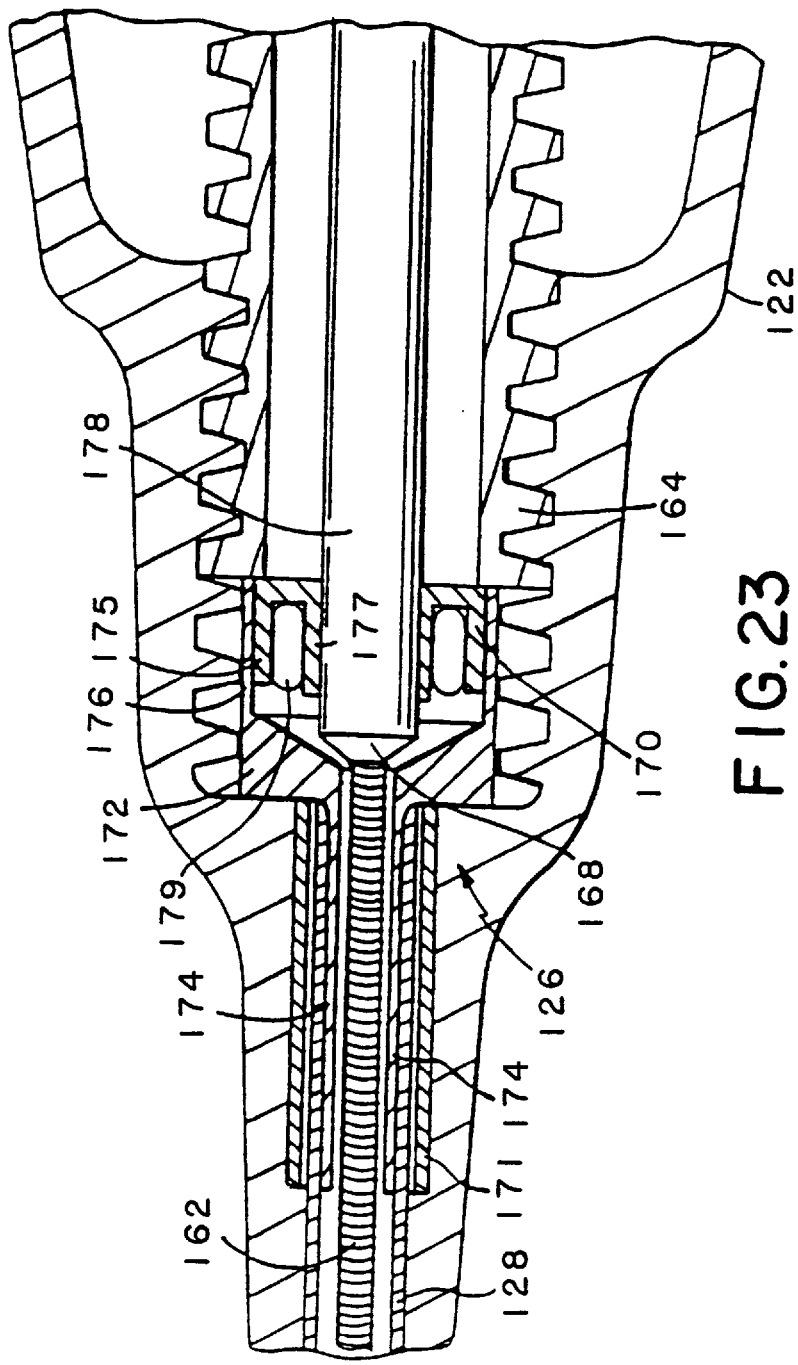
FIG. 23 is an expanded longitudinal cross-sectional view of the proximal end of the catheter coupling of the acoustic imaging balloon catheter of FIG. 22, in partial cross-section.

Referring to FIG. 23, proximally, the catheter of FIG. 22 is provided with a stationary pressure tight shaft seal 126 that fits in intimate, but relatively frictionless contact with a portion of the rotating drive shaft 162. The seal includes a ball seal 170 (available from Bal-seal Engineering Company, Inc., Santa Anna, Calif.), securely held in place by a seal holder 172 (stainless steel or elastomer), which abuts the distal end of the internal open area of the boot 122 and is held by compression of the ferrule assembly 164 (although other means of attachment such as injection molding are possible). The seal holder 172 includes a retainer sleeve 174 that extends coaxially with respect to the catheter 139. At the proximal end, within the ferrule, the drive shaft is held within a gland 178, preferably formed from hypotubing, which makes relatively frictionless contact with the ball seal 170, enabling rotation while preventing back flow of inflation fluid into the ferrule. The ball seal, as shown, is an annular U-shaped member, including within the U a canted coil spring 179 (such that the axis of each coil is tangent to the annulus) that presses the legs 175, 177 of the seal radially. The outer leg 175 of the seal engages an extension 176 of the seal holder, while the inner leg 177 of the seal engages the gland 178. The boot also includes a thin (few thousands of an inch) metal sleeve 171 for additional sealing around the catheter.

The drive shaft 162 is modified in the sealing area 168 by impregnating it with a thermoplastic material that fills the gaps in the individual wires to prevent flow of inflation fluid through the drive shaft inner lumen. Alternatively, the drive shaft may be sealed by impregnating it with a liquid that is hardenable, such as epoxy, and then covering that area with a section of cylindrical metal, such as hypotube, in order to form a smooth, fluid tight seal. It will also be understood that other sealing members may be used, e.g. an O-ring.

Preparation of the device is accomplished by the following steps: A Leveen inflator is connected to the side arm. The side arm valve is opened and air is evacuated by suction. Generally, the balloon contracts in a folded manner which leaves air passages through the interior of the balloon. A hypodermic syringe fitted with a small gauge needle and filled with a fluid such as water or saline is then inserted through a septum seal at the distal tip of the catheter sheath. Fluid is introduced until surplus exits the side arm, at which point the valve is closed, reducing the chances that air will re-enter the catheter. Alternately, the fluid may be introduced via the side arm when an air venting needle is inserted into the distal septum.

The catheter is then attached to the driving motor, (not shown), by mating the ferrule 124 with a mateable receptacle that connects it to the ultrasound imaging electronics. Because the balloon material and sonolucent guide effectively transmit ultrasound energy, continuous imaging and monitoring can be achieved.

The pressure and fluid tight connector that is mounted distally to the location of the side arm connector enables various catheters, such as those with balloons of different sizes, to be effectively attached at the location of the side arm connector.

In other embodiments, the transducer may be positioned proximal to the balloon.

Figure 26:
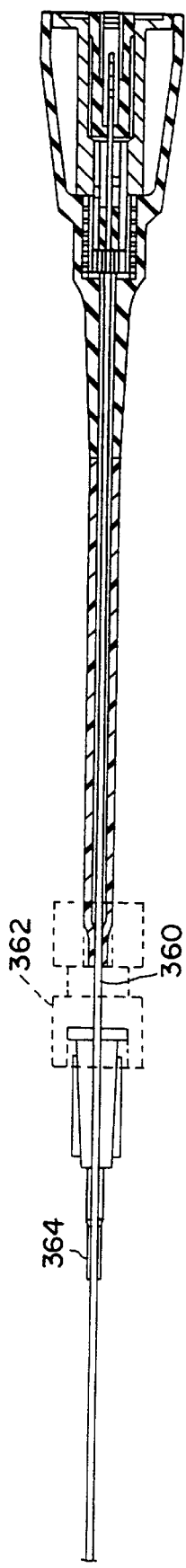
Figure 25:
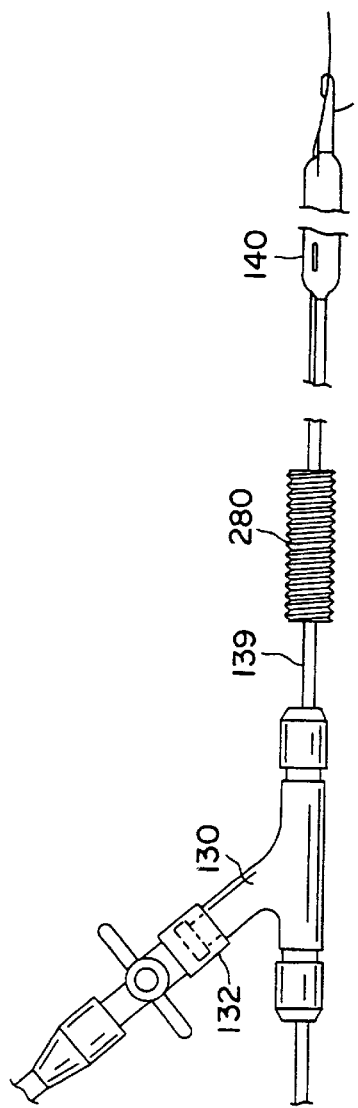

Referring now to FIGS. 24, 25, and 26, other embodiments of the acoustic imaging catheter device allow relative movement of the transducer and balloon so that the ultrasound transducer may be positioned in any longitudinal position in the balloon, or distal or proximal to the balloon. The embodiments shown in FIGS. 24, 25, and 26 may include all of the features of the catheter system shown in FIGS. 19–19c, including one or more electrodes for electrophysiology or ablation mounted on the catheter sheath, and may include all of the features of the catheter system shown in FIGS. 22 and 23. Moreover, the features shown in FIGS. 24, 25, and 26 may be used in conjunction with any of the catheter sheaths disclosed in this application, including catheter sheaths that do not include balloons and including all of the catheter sheaths on which electrophysiology or ablation electrodes are mounted. In FIG. 24, the drive shaft and transducer 146 may be slid axially as indicated by arrows 195 to move the transducer, for example, continuously to positions between position I, proximal to the balloon and position II, distal to the balloon. A slide assembly 240 is provided including a housing 244 having a distal end which receives the catheter sheath 139 and drive shaft 145. The drive shaft contacts a pair of oppositely arranged, relatively frictionless ball seals 245, 246 press fit within the housing against an inner body extension 249 and the distal end member 248 of the body which is threaded into the body 244. The ball seals engage a gland 250 as discussed with respect to FIG. 23. The gland is attached to a thumb control 252, provided within the body to enable axial motion of the drive shaft to position the transducer within the catheter corresponding to regions within the balloon and in the distal extension, both of which are sonolucent.

The axially translatable transducer device further includes a carbon resistor 254 within the slide assembly housing, and contact means 258 attached to the thumb control and in contact with the resistor. Probe wires 256, 257 are connected to the resistor 254 and contact means 258 to provide variable resistance between the probe wires as the thumb control is slid axially, which is detected at detector 260, to provide monitoring of the axial position of the transducer. The thumb control may be hand actuated or controlled by automatic translator means 264 which receives control signals from a controller 266. The output from the detector 260 may be provided to an analysis means 268 which also receives the acoustic images from the transducer corresponding to various axial positions of the transducer within the catheter body to provide registry of the images with the axial transducer position on a screen 270. In certain embodiments, the transducer is slid axially, along a continuous length or at selected positions of the catheter body, for example, from the balloon to the distal tip, and the analysis means includes storage means for storing images along the length to reconstruct a three-dimensional image of the lumen along the axial length of transducer travel.

FIG. 25 shows an embodiment in which the catheter includes a bellows member 280 to enable axial motion of the catheter body with respect to the transducer.

FIG. 26 shows an embodiment in which a proximal portion of the drive shaft is enclosed within tubing 360, which is engaged by a user-graspable housing 362 that is attached to the proximal end of catheter sheath 364. The user can push tubing 360 into housing 362 and can pull it out of housing 364 to adjust the relative longitudinal position of the transducer on the end of the drive shaft with respect to catheter sheath. User-graspable housing 362 engages tubing 360 by means of a fluid-tight seal.

In another embodiment of the acoustic imaging catheter device, the balloon is asymmetrical, either in shape or expansion capability, or both, and is mounted on a catheter shaft that is torquable, and can be positioned using acoustic imaging. The positioning of the balloon relative to surrounding tissue and the inflation and deflation of the balloon can be monitored with cross-sectional ultrasonic images.

Figure 27:
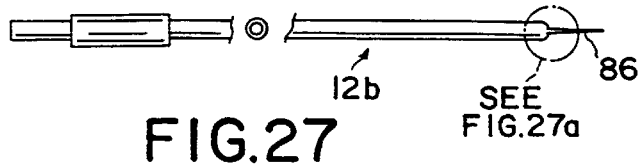
FIG. 27 is a longitudinal view of an acoustic imaging catheter sheath having a hollow needle, extending from the distal tip of the catheter sheath, for injection of fluid into cardiac tissue.
Figure 27A:
FIG. 27a is a detailed cross-sectional view of the distal tip of the catheter sheath shown in FIG. 27.

FIGS. 27 and 27a show sheath 12b having needle 86 securely anchored to the tip, useful for impaling a surface, such as that found in the interior of the heart, and injecting chemicals such as ethanol into the heart. Needle 86 can also be used to anchor temporarily and steady the ultrasound device in a fixed position. In another embodiment, it can have a safety wire extending to a proximal securing point. This acoustic catheter may be introduced through an introducing catheter. In another embodiment, the needle can be retracted during introduction.

Figure 28:
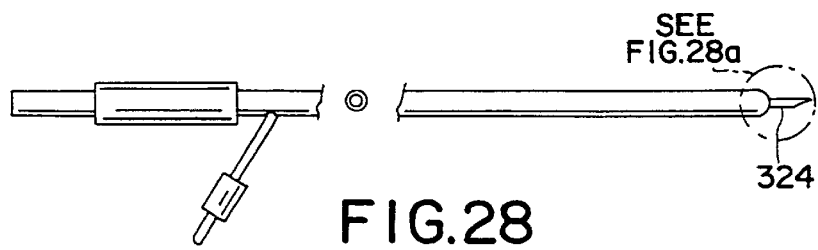
FIG. 28 is a longitudinal view of an acoustic imaging catheter sheath having a needle, extending from the distal tip of the catheter sheath, constructed of an electrically excitable material that generates acoustic energy when excited.
Figure 28A:
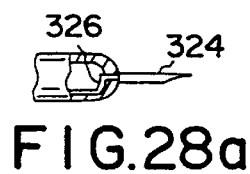
FIG. 28a is a detailed, partially cross-sectional view of the distal tip of the catheter sheath shown in FIG. 28.

FIGS. 28 and 28a show a solid needle 324 made of an electrically excitable material that emits acoustic energy when excited through conductor 326 by RF electrical signals applied to electrical terminal 328. Vibration of needle 324 creates a massaging action that disrupts tissue and creates an ablative response.

In an alternative embodiment, needle 324 is hollow, and the vibration of the needle assists the process of injecting the drug into the tissue. The hollow metal is covered with a shrink of polyvinylidene fluoride, and the polyvinylidene fluoride is aluminized over its outside. This construction produces an assembly that vibrates when electrically excited. The purpose of the aluminum is to conduct electric power. The aluminum can be seen in the image formed by means of the ultrasound transducer, and it can also serve as an acoustic marker that can be seen by an external ultrasound device or an ultrasound probe placed a distance away from the ablation catheter.

Figure 29:
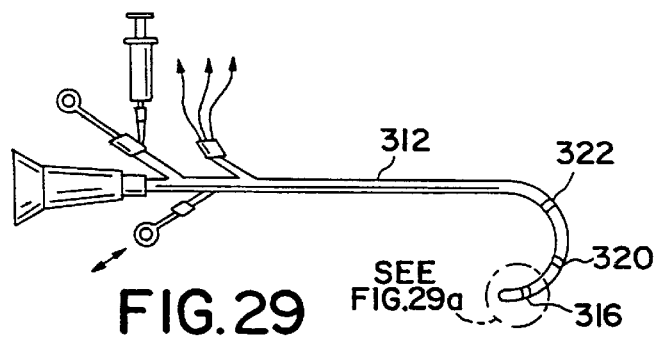
FIG. 29 is a perspective view of an acoustic imaging catheter sheath having a hollow needle, extending from a side wall of the catheter sheath, for injection of fluid into cardiac tissue, and having electrodes for electrophysiology or cardiac ablation mounted on the catheter sheath.
Figure 29A:
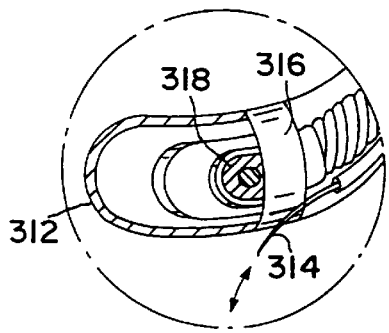
FIG. 29a is a detailed, partially cross-sectional view of the distal tip of the catheter sheath shown in FIG. 29.

FIGS. 29 and 29a show steerable catheter sheath 312, capable of electrophysiology sensing and acoustic imaging, in which the tip of retractable injecting needle 314 exits catheter sheath 312 near the tip of the catheter sheath and also near ring electrode 316 and the position of the scan plane of transducer 318. Visualization of the location of the electrode can be performed under ultrasound guidance, and then the needle can be extended into the endocardium to inject fluid into the endocardium. Electrode 316 is the most distal of several electrodes 316, 320, and 322. Ring electrode 316 may be of a conventional type that can be located with ultrasound. In another embodiment electrode 316 is a tip electrode rather than a ring electrode.

In one embodiment, the longitudinal position of the transducer is adjustable, in accordance with any of the techniques described above in connection with FIGS. 24, 25, and 26. In another, simpler embodiment, transducer 318 is located permanently in a fixed longitudinal location at which the plane of acoustic imaging intersects the needle when the needle at the beginning of its extended position.

In use, the catheter is put into position in the heart with needle 314 retracted, a site that is suspected of electrical malfunction is probed with the steerable catheter under ultrasound visualization, and electrical potentials are read and recorded. Once a specific location is found that appears to be problematic, ablation can then be performed by deploying the needle and the needle can inject the tissue with an ablative drug such as ethanol. The needle can penetrate 2–3 millimeters if necessary. The catheter can be left in position during this time and a change in the electrical properties of the tissue can be monitored.

In another embodiment, a highly conductive wire, such as gold-plated metal or gold-plated stainless steel, can be used in place of the needle. The wire ablates tissue in a manner analogous to the ablation electrodes described above, but the wire can be used to anchor the catheter and could be curved to pull the electrode into position to enhance the electrical ablation. The wire can include an acoustic marker that can be seen by an external ultrasound device or an ultrasound probe placed a distance away from the ablation catheter.

Figure 30:
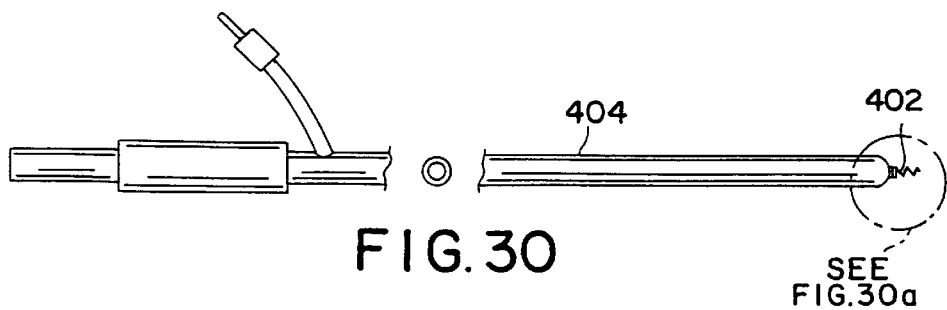
FIG. 30 is a longitudinal view of an acoustic imaging catheter sheath having a wire in the shape of a cork screw attached to its distal end.
Figure 30A:
FIG. 30a is a detailed, partially cross-sectional view of the distal tip of the catheter sheath shown in FIG. 30.
Figure 31:
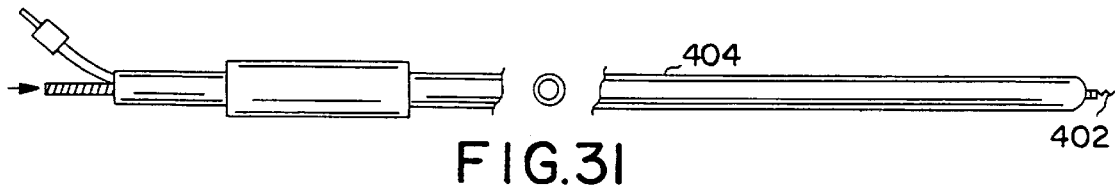
FIG. 31 is a longitudinal view of an acoustic imaging catheter sheath having a wire in the shape of a cork screw passing through its distal end, the wire being attached to the drive shaft within the sheath.
Figure 31A:
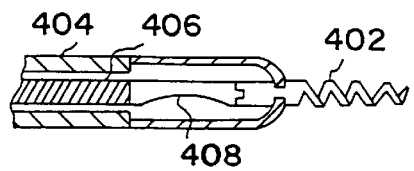
FIG. 31a is a detailed, partially cross-sectional view of the distal tip of the catheter sheath shown in FIG. 31.

In certain embodiments, shown in FIGS. 30, 30a, 31, and 31a, the wire is formed as a little cork screw 402 that can be twisted into the heart, in a manner similar to twisting a pacing lead into the heart, to anchor the tip of catheter sheath 404 very securely under ultrasound guidance. FIGS. 30 and 30a show cork screw 402 directly attached to catheter sheath 404. In this embodiment cork screw 402 is twisted into heart tissue by rotating the entire catheter. FIGS. 31 and 31a show cork screw 402 directly attached to drive shaft 406, distally beyond transducer 408. In this embodiment cork screw 402 is twisted into heart tissue by rotating drive shaft 406. In other embodiments, the corkscrew is attached to an elongated, torsionally rigid but laterally flexible assembly, similar to the ultrasound imaging driveshaft but much smaller in diameter, so that the corkscrew can be automatically caused to turn and corkscrew into tissue. The corkscrew exits a small hole in the catheter sheath in the same manner as needle 314 described above, but the corkscrew follows a curved path.

Figure 32:
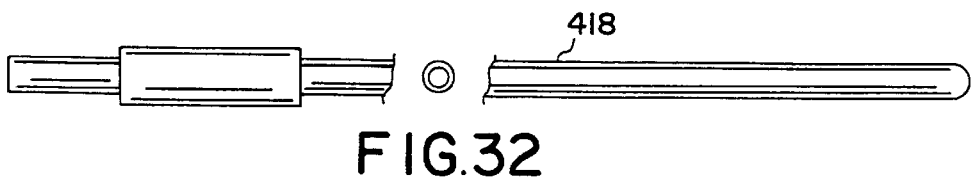
FIG. 32 is a longitudinal view of an acoustic imaging catheter sheath enclosing a drive shaft on which an imaging transducer and an ablation transducer are mounted.
Figure 32A:
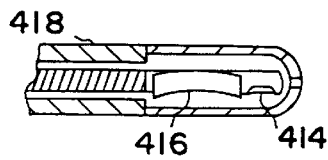
FIG. 32a is a detailed, partially cross-sectional view of the distal tip of the catheter sheath shown in FIG. 32.

Referring to FIGS. 32 and 32a, in catheter sheath 418, an ultrasound transducer 414 is used to ablate tissue sonically. Ultrasound transducer 414 is similar to, and located adjacent to, ultrasound imaging transducer 416 of the type described in detail above. Transducer 416 images by rotating a full 360 degrees while catheter sheath 418 is in a fixed position or a relatively stationary position, the image is stored, and then the rotation of the transducer is stopped and the position of transducer 414 is aligned, based on the stored image, so that transducer 414 is pointed toward the region of interest. During ablation, transducer 414 radiates at least 2–5 watts of acoustic power at a frequency of around 25 to 50 kilohertz. This frequency that is so low that the radiation is not focused, but instead tends to radiate from the source in a more or less cardioid pattern without a fixed focus. The energy has its greatest density normal to the surface of transducer 414.

In another embodiment the ablation transducer is positioned in a manner such that it directs radiation in a direction 180 degrees away from the direction in which the imaging transducer directs ultrasound energy, and the ablation transducer and imaging transducer are at the same longitudinal location. The ablation transducer can be aligned in the desired direction for ablating tissue by positioning the imaging transducer in a manner such that the imaging transducer is facing 180° away from the region of interest to be ablated. In yet another embodiment a single transducer is capable of both imaging and very high-power, low-frequency radiation.

Figure 33:
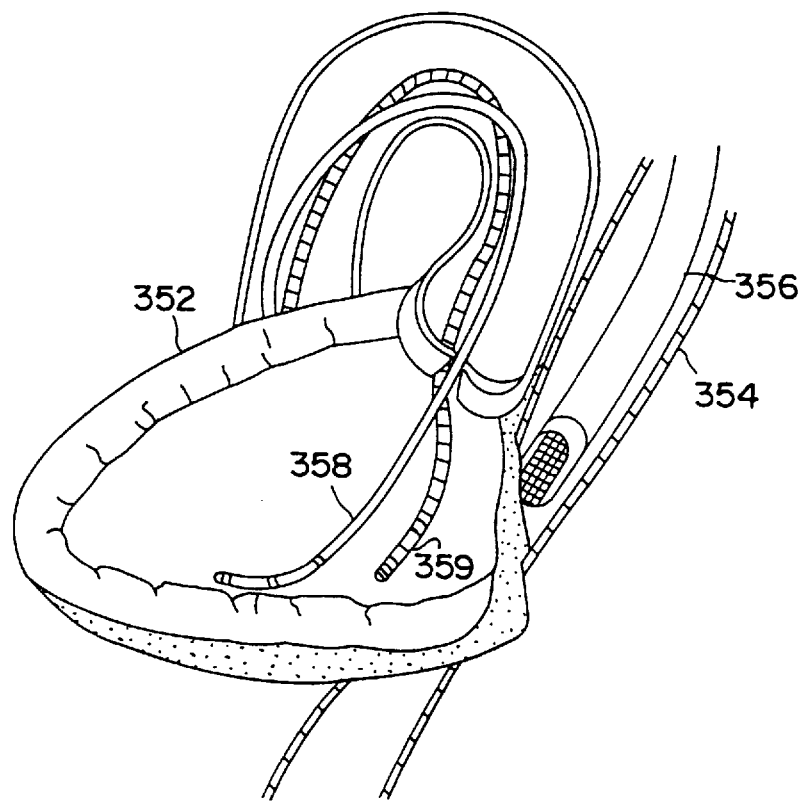
FIG. 33 is a partially cut-away view of a heart and a portion of an esophagus, showing the use of a transesophageal probe in combination with two catheters whose distal portions are located within a heart chamber.

FIG. 33 illustrates an alternative imaging mode that is useful in conjunction with the needle-equipped and balloon-equipped catheters for chemical ablation described above, and also even the electrode-equipped catheters described above, if the electrodes are fitted with polyvinylidene fluoride coverings. According to this imaging mode, the heart 352 is imaged through the esophagus 354, by means of one of many commonly available trans-esophageal probes 356 such as those made by Hewlett Packard, Vingmead and others. This trans-esophageal imaging provides a cross-sectional image of the heart, i.e., a scan plane that is a slice of the heart. Various improved transesophageal probes can vary the plane scanned through the heart through various angles and various rotational and azimuthal positions, and can therefore be used to image a very wide area of the heart through manipulation of controls on the proximal end of the transesophageal probe. During use, transesophageal probe 356 is first placed in a patient's esophagus prior to the beginning of an electrophysiology procedure, and electrophysiology or ablation catheters 358 and 359 are then placed in the heart through the venous or the arterial system. These catheters can be visualized by means of esophageal probe 356 if the catheters are fitted with acoustic markers.

The marker may be, for example, a PVDF covering placed over a sensing or ablation electrode, or a PVDF balloon. The acoustic markers are used to create distinct color artifacts on the image created by color flow imaging machines equipped with color capability. The color flow display is a black and white display that has a graphic overlay of flow information, which is denoted by a color shown on the CRT display. When the PVDF is electrically excited it emits a low-frequency sonic wave that is misinterpreted by the trans-esophageal imaging system as the difference between the outgoing ultrasound pulse and the Doppler-shifted return pulse that the trans-esophageal system uses to deduce the direction and quantity of blood flow (the imaging system determines blood flow by measuring the difference between the outgoing and the incoming ultrasound signal and assigning a false color to the frequency shift that occurs due to the Doppler effect). Thus, by radiating at a frequency near the expected Doppler shift frequency, the PVDF basically fools the trans-esophageal imaging system into thinking the low-frequency sonic wave is the difference signal and can induce the imaging system to show false colors that identify particular catheters. A catheter shows up on the display as either a bright mark or dot that represents the cross-section of the catheter. To energize the PVDF a sinusoidal, continuous-wave, voltage signal is applied to the PVDF through a simple, alternating-current, radio-frequency generator. This signal can be pulsed as well, if desired.

One or more of the intra-cardiac catheters may include an ultrasound transducer, which may be adjacent to or at the precise location of sensing and ablation electrodes, as described above. Vacuum-deposited traces may extend along the length of the catheter sheath to the electrodes, as described above. The traces provide good electrical coupling and can serve as an attachment point for PVDF or a crimped-on transducer. The incorporation of the traces into the wall of the catheter sheath leaves the bore of the catheter free to be used for a pacing lead, an anchoring screw, a drug injection channel, a biopsy channel, etc.

In one embodiment, an entire catheter sheath is made of PVDF. The catheter sheath will show up on the display no matter which portion of the catheter sheath intersects with the imaging plane of the transesophageal probe, because the whole catheter sheath emanates radiation. In another embodiment, a first catheter used during the procedure emits a frequency that shows up as a first color on the color flow imaging, a second catheter emits a frequency that shows up as a second color, and so on. In another embodiment the tip or the actual electrode portion of a catheter sheath has a frequency that is distinct from the rest of the catheter sheath, so that when the tip or the electrode is located by the imaging system it is distinguishable from the remainder of the catheter sheath. In another embodiment, there is a graduation in frequency along the length of a catheter, so that a distal tip shows up as a first color, a midsection shows up as a second color, and a proximal section shows up as a third color. The change in frequency along the length of the catheter may be gradual or may be in the form of distinct stripes of different frequencies.

Figure 34:
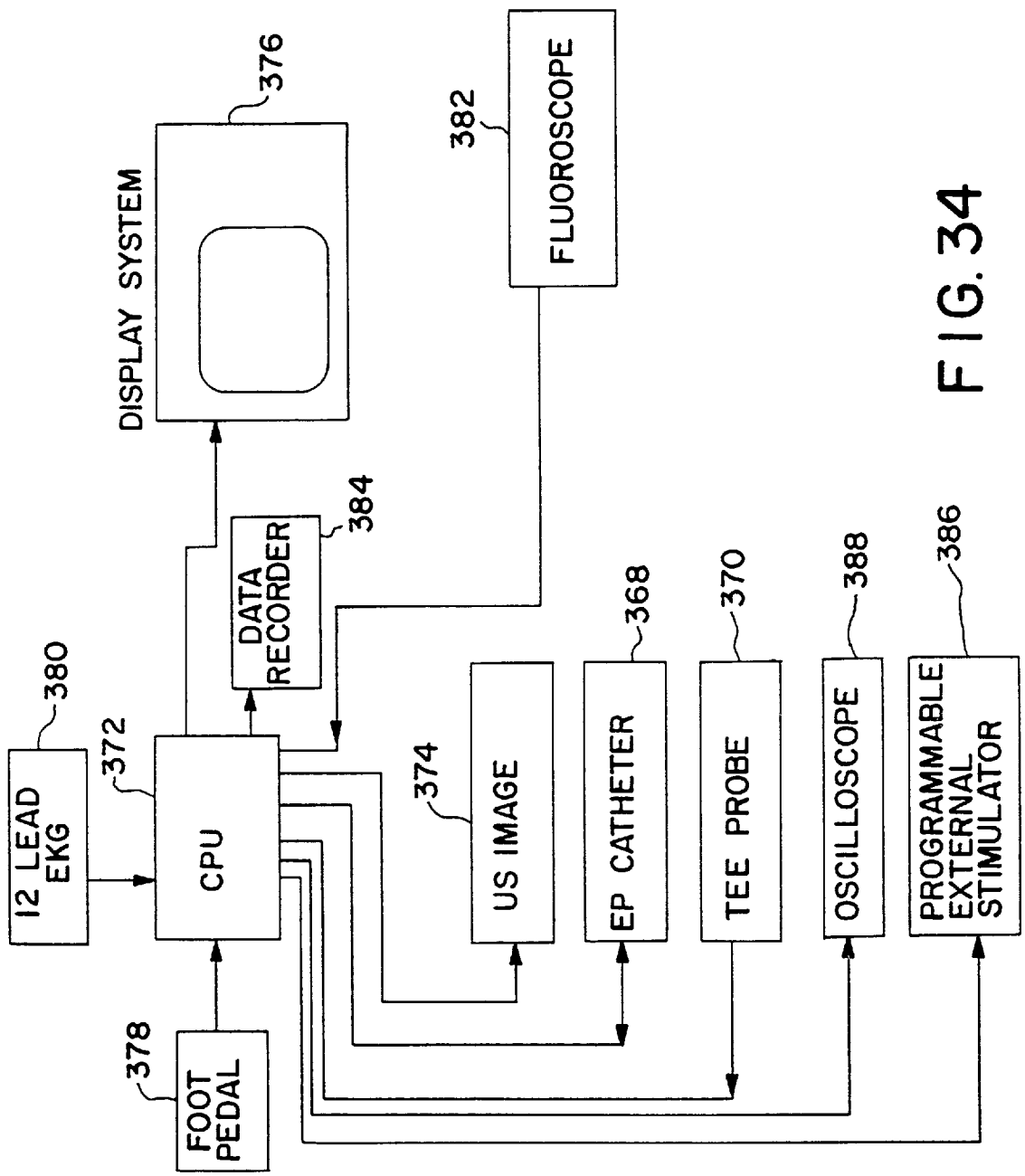
FIG. 34 is a block diagram of the principle components of an acoustic imaging and electrophysiology system that includes an electrophysiology catheter and a display that super-imposes electrophysiology data on an image of the heart.

FIG. 34 illustrates a system of electrophysiology equipment that includes an acoustic imaging electrophysiology catheter 368 of the type shown in FIG. 13, a transesophageal probe 370, a central processing unit 372 that receives data from catheter 368 or trans-esophageal probe 370 and transmits video ultrasonic image data to ultrasound display 374, and another display system 376 that displays, either graphically, schematically, or with a wire frame, specific regions of the heart, and that records and displays on a specific location of the graphical, schematic, or wire frame display either an instantaneous voltage or a voltage throughout an entire cardiac cycle.

In one embodiment, display system 376 displays a two-dimensional cross-sectional image of the heart, which shows important features of the heart such as the area of the HIS bundle. The cross-sectional image is based on ultrasound image received from catheter 368 or trans-esophageal probe 370 or is based on a fluoroscopic image from fluoroscope 382. Other possible sources of the cross-sectional image include MRI, CT, and scintigraphy. When catheter 368 is placed in specific regions of the heart, which can be done with great certainty because of the ultrasound imaging capability, the voltage potentials sensed by catheter 368 are recorded instantaneously by central processing unit 372 and then displayed in the specific locations in the graphic. Many voltage potentials are sensed at various locations in the heart until an electrophysiological map of the heart is built up, which can be done very quickly.

Because the user or the clinician will want to concentrate on maneuvering the catheters, and not on data acquisition, writing information down, or shouting out numbers, a foot pedal 378 is provided so that when catheter 368 is in a specific location the clinician can depress foot pedal 378 to instruct central processing unit 372 to record voltage potential information. Because central processing unit 372 receives ultrasound imaging data, central process unit 372 knows the specific location of each electrophysiology electrode and thus knows the location at which to super-impose voltage data on the image shown by display system 376. Alternatively, the clinician can observe the image displayed by display system 374 and can indicate to central processing unit 372 the specific location of an electrode.

Thus, central processing unit 372 records both an ultrasonic image at a particular instant and a voltage values at that instant and at a particular location. Thus, the clinician can return the sensing electrode to the particular location at a later point in time to compare the voltage sensed at the later point in time with the earlier-recorded voltage.

Moreover, the information recorded by central processing unit 372 permits analysis of various voltage potentials throughout a cardiac cycle as the heart moves during the cycle, because central processing unit 372 is able to keep track of the various locations in the heart even though the heart is moving.

A set of electrocardiogram or EKG leads 380 are connected to central processing unit 372. In one embodiment, when the clinician wants to record a voltage potential, central processing unit 372 records the voltage information throughout one complete cardiac cycle. The clinician can view a representation of the voltage at any instance in time during the cardiac cycle by replaying the image displayed by display system 376 with the super-imposed voltage information. Central processing unit 372 processes ultrasound imaging information and voltage information in the manner of a cine loop or repeating image, which is gated by EKG leads 380 attached to the patient while the patient is left in a still position. The central processing unit causes display system 376 to display a series of successive frames in a loop that repeats over and over again. In one embodiment there are 32 ultrasound imaging frames that go through one complete cardiac cycle from systole to diastole and back to systole, and there are 32 different voltages that are super-imposed on the ultrasound imaging frames at any given location. The super-imposed voltage information at a given location is a number that rises and falls throughout the cardiac cycle, or is alternatively a color coded mark. Thus, there is no need to image the heart continuously, which could take up a lot of software and hardware time, and yet display system 376 displays an image of the heart timed in exact synchronization with the actual heart beating (through use of EKG leads 380) and replayed over and over again. While this image is being replayed, the clinician can concentrate on simply locating the position of catheter 368 itself in the heart and can follow the catheter with trans-esophageal echo probe 370, or through x-rays because catheter 368 is marked with radiopaque markers.

Any additional information that the clinician obtains while the image is being replayed can be super-imposed over the repeating image without the need to re-image the heart. For example, a live fluoroscopic or ultrasound image can be super-imposed over the image being replayed on display system 376. If the super-imposed live image is a fluoroscopic image, it is not necessary to use dye injection while obtaining this live image because the location of the heart tissue relative to the catheter 368 can be seen on display system 376 without any need for the live image itself to show the heart. If the clinician wishes, however, he may update the image by obtaining a new image of the heart, if the patient has moved or if the clinician believes that the heart has changed position or has changed its cycle.

In another embodiment, the display system 376 displays a false three-dimensional image of the heart or a true three-dimensional image of the heart. A false three-dimensional image of the heart is a three-dimensional projection onto a two-dimensional surface that can be generated using commonly available computer imaging hardware and software that takes a number of successive two-dimensional images and assembles them into a false three-dimensional image that can be rotated and manipulated by the user by the user interfacing with central processing unit 372. False three-dimensional ultrasound images can be obtained through the use of accessory software and hardware such as that provided by ImageComm in Sunnyvale, Calif. A true three-dimensional is an image that is not displayed on a flat screen but rather on an oscillating mirror that has a scanning system associated with it that can display a three-dimensional image by stereoscopic means. It is not necessary to wear stereoscopic glasses to view oscillating mirror systems that are currently being marketed.

Alternatively, display system 376 may display a wire-frame image, which is a graphical depiction of the boundaries of the heart and is a simple version of a false 3-dimensional image. The beauty of a wire frame image is that it requires relatively less software and hardware to display and is inherently transparent or translucent so that potentials can be seen through it intuitively by the user. Also, a wire-frame images does not require a large amount of hardware or software to rotate and manipulate the image. The nodal points, i.e. the places where the wires cross, can be used as the data collection points.

One of the very important aspects of the electrophysiology procedure is that once the operation of the heart is diagnosed, the clinician will want, as precisely as possible, to position an ablation device at the source of trouble and ablate the tissue at this location precisely. This requires relocalization of the tip of catheter 368 to a previously located position. All positions at which the catheter tip has been positioned are accurately located on the display of display system 376, and the clinician can determine when the tip of catheter 368 has been relocated by examining the ultrasound image. Thus, the clinician can return to the spot to be ablated with a great degree of confidence.

In one embodiment, trans-esophageal probe 370 creates ultrasound images that are processed by central processing unit 372 and displayed by display system 376, and the ultrasound transducer on catheter 368 is used to create an image displayed on display system 374 to assure good contact of electrodes with tissue. Alternatively, a general sense of the catheter position is obtained through the use of an imaging modality such as fluoroscope 382, and a more precise image is obtained by trans-esophageal probe 370 or the ultrasound transducer on catheter 368 and is processed by central processing unit 372 to create the display for display system 376.

The electrophysiology catheters described in detail above are especially useful for creating an accurate two-dimensional, three-dimensional, or wire-frame image because these catheters are highly maneuverable by their ability to deflect or to be positioned with the assistance of a positioning balloon, because the transducer within these catheters is highly accurate in identifying the position of the catheter relative to tissue, and because these catheters are easily recognizable in trans-esophageal images.

A data recorder 384 is provided in the system of electrophysiology equipment shown in FIG. 34 to record data from EKG leads 380 and the electrophysiology electrodes on catheter 368 in tabular form for analysis. An oscilloscope 388 displays signals from each of the electrophysiology electrodes on catheter 368. A programmable external stimulator 386 is used to provide slight electrical pulses to electrodes on catheter 368 to cause fibrillation so that the action of the heart can be observed while the heart is in this condition.

Other embodiments are within the claims. For example, it is contemplated that each of the various selectable catheter sheaths may incorporate any of the features shown or described in connection with one or more of the other selectable catheter sheaths. Furthermore, the ultrasound transducer described above may be used in conjunction with catheter sheaths incorporating the features of any of the catheters described in either of the following two U.S. patent applications, which are being filed on the same day as the present application, and the disclosures of which are hereby incorporated in their entirety herein: "Ablation Catheters," by Charles D. Lennox et al., and "Heart Ablation Catheter with Expandable Electrode" by John E. Abele.

Figure 35:
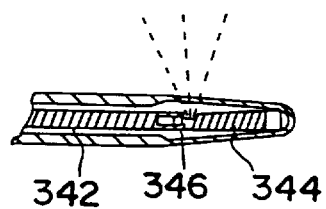
FIG. 35 is a cross-sectional view of a catheter having a rotatable-drive shaft on which a mirror is mounted, the mirror being configured to reflect ultrasound signals produced by a transducer.

It is contemplated that each of the various selectable catheter sheaths may be used in conjunction with any of the technologies shown in FIGS. 24, 25, and 26 for enabling relative longitudinal movement between the transducer and the catheter sheath during use of the catheter. Also, each of the various selectable catheter sheaths may be used in conjunction with a drive shaft of the type shown in FIG. 35, in which drive shaft 342 has a rotating mirror 344 on its distal end that reflects an ultrasound signal emitted by an ultrasound transducer 346, which may also be attached to drive shaft 342 as shown or alternatively may be fixed in a stationary position while the drive shaft rotates.

What is claimed is:

1. A catheter system, comprising:

an elongated, flexible catheter constructed to be inserted into a body of a living being;

an imaging system constructed and arranged to provide information from which a graphical representation of an internal structure within said body of said living being may be created, said imaging system comprising an ultrasound device incorporated into said elongated, flexible catheter, a data collection system, at least partially located on a distal portion of said elongated, flexible catheter, constructed and arranged to produce a plurality of items of data corresponding to a respective plurality of locations within said internal structure, a central processing unit, electrically connected to said imaging system and said data collection system, said central processing unit configured and arranged to simultaneously record said information provided by said imaging system and said plurality of items of data provided by said data collection system, to create said graphical representation of said internal structure from said information provided by said imaging system, and to super-impose onto said graphical representation said plurality of items of data provided by said data collection system, said plurality of items of data being super-imposed at locations on said graphical representation that represent said respective plurality of locations within said internal structure corresponding to said plurality of items of data, and a graphic display system, electrically connected to said central processing unit, and constructed to display said graphical representation onto which said plurality of items of data are super-imposed.

2. A catheter system in accordance with claim 1, wherein said ultrasound device is arranged to direct ultrasonic signals towards an internal structure within said body of said living being for the purpose of creating an ultrasonic image of said internal structure, said graphical representation comprising said ultrasonic image.

3. A catheter system in accordance with claim 1, wherein said data collection system comprises an electrophysiology electrode mounted on said distal portion of said elongated, flexible catheter, said electrophysiology electrode being constructed to sense electrical potentials within said internal structure when said electrode is placed in electrical contact with said internal structure.

4. A catheter system in accordance with claim 1, wherein said items of data collected by said data collection system comprise identifications of locations within said internal structure at which said distal portion of said elongated, flexible catheter is positioned.

5. A catheter system in accordance with claim 1, wherein said items of data are portions of an image super-imposed on said graphical representation.

6. A catheter system in accordance with claim 1, wherein said graphical representation comprises a two-dimensional cross-sectional image of said internal structure.

7. A catheter system in accordance with claim 1, wherein said graphical representation comprises a false three-dimensional image of said internal structure.

8. A catheter system in accordance with claim 1, wherein said graphical representation comprises a true three-dimensional image of said internal structure.

9. A catheter system in accordance with claim 1, wherein said graphical representation comprises a wire-frame representation of said internal structure.

10. A catheter system in accordance with claim 1, wherein each of said plurality of items of data corresponds to one of at least two points in time, and is super-imposed on said graphical representation at a time that represents said one of said at least two points in time.

11. A catheter system in accordance with claim 10, wherein said graphical representation comprises a repeating representation of said internal structure.

12. A catheter system in accordance with claim 11, wherein said repeating representation of said internal structure is synchronized with input received from an EKG system.

13. A catheter system in accordance with claim 1, wherein said central processing unit is configured to super-impose a live image over said graphical representation of said internal structure.

14. A catheter system in accordance with claim 1, wherein said items of data collected by said data collection system comprise physiological data for the internal structure corresponding to a respective plurality of locations within said internal structure.

15. A catheter system, comprising:

an elongated, flexible catheter constructed to be inserted into a body of a living being, an imaging system constructed and arranged to provide information from which a graphical representation of an internal structure within said body of said living being may be created, said imaging system comprising a trans-esophageal ultrasound imaging device, a data collection system, at least partially located on a distal portion of said elongated, flexible catheter, constructed and arranged to produce a plurality of items of data corresponding to a respective plurality of locations within said internal structure, a central processing unit, electrically connected to said imaging system and said data collection system, said central processing unit configured and arranged to simultaneously record said information provided by said imaging system and said plurality of items of data provided by said data collection system, to create said graphical representation of said internal structure from said information provided by said imaging system, and to super-impose onto said graphical representation said plurality of items of data provided by said data collection system, said plurality of items of data being super-imposed at locations on said graphical representation that represent said respective plurality of locations within said internal structure corresponding to said plurality of items of data, and a graphic display system, electrically connected to said central processing unit, and constructed to display said graphical representation onto which said plurality of items of physiological data are super-imposed.

16. A catheter system in accordance with claim 15, wherein said graphical representation comprises an ultrasonic image created by said trans-esophageal ultrasound imaging device.

17. A catheter system in accordance with claim 15, wherein said data collection system comprises an electrophysiology electrode mounted on said distal portion of said elongated, flexible catheter, said electrophysiology electrode being constructed to sense electrical potentials within said internal structure when said electrode is placed in electrical contact with said internal structure.

18. A catheter system in accordance with claim 15, wherein said items of data are portions of an image super-imposed on said graphical representation.

19. A catheter system in accordance with claim 15, wherein said graphical representation comprises a two-dimensional cross-sectional image of said internal structure.

20. A catheter system in accordance with claim 15, wherein said graphical representation comprises a false three-dimensional image of said internal structure.

21. A catheter system in accordance with claim 15, wherein said graphical representation comprises a true three-dimensional image of said internal structure.

22. A catheter system in accordance with claim 15, wherein said graphical representation comprises a wire-frame representation of said internal structure.

23. A catheter system in accordance with claim 15, wherein each of said plurality of items of data corresponds to one of at least two points in time, and is super-imposed on said graphical representation at a time that represents said one of said at least two points in time.

24. A catheter system in accordance with claim 15, wherein said graphical representation comprises a repeating representation of said internal structure.

25. A catheter system in accordance with claim 15, wherein said central processing unit is configured to super-impose a live image over said graphical representation of said internal structure.

26. A catheter system in accordance with claim 15, wherein said items of data collected by said data collection system comprise identifications of locations within said internal structure at which said distal portion of said elongated, flexible catheter is positioned.

27. A catheter system in accordance with claim 15, wherein said items of data collected by said data collection system comprise physiological data for the internal structure corresponding to a respective plurality of locations within said internal structure.

* * * * *

UNITED STATES PATENT AND TRADEMARK OFFICE
CERTIFICATE OF CORRECTION

PATENT NO. : 5,840,031
DATED : November 24, 1998
INVENTOR(S) : Robert J. Crowley It is certified that error appears in the above-identified patent and that said Letters Patent is hereby corrected as shown below:

Column 9, line 4, please change ".20" to -- 20 --.

Column 12, line 61, please change "the-catheter" to -- the catheter --.

Column 19, line 10, please change "Anna" to -- Ana --.

Column 24, line 46, please change "values" to -- value --.

Column 27, line 4, please change "being;" to -- being, --.

Signed and Sealed this

Fifth Day of December, 2000

Attest:

Q. TODD DICKINSON

*Attesting Officer*  *Director of Patents and Trademarks*